United States Patent [19]
Evans et al.

[11] Patent Number: 5,932,622
[45] Date of Patent: Aug. 3, 1999

[54] METHOD FOR IN VIVO MODULATION OF NON-MALIGNANT SKIN-RELATED PROCESSES WITH 9-CIS-RETINOIC ACID

[75] Inventors: Ronald M. Evans, La Jolla, Calif.; David J. Mangelsdorf, Dallas, Tex.; Richard A. Heyman, Encinitas; Marcus F. Boehm, San Diego, both of Calif.; Gregor Eichele; Christina Thaller, both of Houston, Tex.

[73] Assignees: The Salk Institute for Biological Studies, La Jolla, Calif.; Baylor College of Medicine, Houston, Tex.; Ligand Pharmaceuticals, Inc., San Diego, Calif.

[21] Appl. No.: 08/475,174

[22] Filed: Jun. 7, 1995

Related U.S. Application Data

[62] Division of application No. 08/244,857, Jun. 14, 1994, which is a continuation of application No. PCT/US92/11214, Dec. 18, 1992, which is a continuation-in-part of application No. 07/809,980, Dec. 18, 1991, abandoned.

[51] Int. Cl.⁶ .............................. A61K 31/07; C12N 5/06
[52] U.S. Cl. ...................... 514/725; 514/863; 514/864; 435/325
[58] Field of Search .................................. 514/256, 725, 514/880, 863, 864; 435/240.1, 325

[56] References Cited

U.S. PATENT DOCUMENTS 5,192,534   3/1993   Grollier et al. ........................ 424/59

FOREIGN PATENT DOCUMENTS 2641184   7/1990   France .

OTHER PUBLICATIONS

Mezick et al. (1984) *J. Investigat. Dermatol.,* (83)2, "Topical and Systemic Effects of Retinoids on Horn–Filled Utriculus Size in the Rhino Mouse. A Model to Quantify 'Antikeratinizing' Effects of Retinoids", pp. 110–113.

Brockes (1990) *Nature,* 345, "Reading the Retinoid Signals", pp. 766–768.

Lehmann et al. (1992) *Science,* 258, "Retinoids Selective for Retinoid X Receptor Response Pathways", pp. 1944–1946.

Levin et al. (1992) *nature,* 355, "9–Cis Retinoid Acid Stereoisomer Binds and Activates the Nuclear Receptor RXRα", pp. 359–361.

*Primary Examiner*—Jon P. Weber
*Attorney, Agent, or Firm*—Stephen E. Reiter; Gray Cary Ware & Freidenrich LLP

[57] ABSTRACT

A method for modulating non-malignant skin related disorders in a subject has been demonstrated with 9-cis retinoic acid. Wrinkling, acne, keratinization, differentiation and proliferation disorders are treated by administration of 9-cis retinoic acid alone or in a pharmaceutically acceptable carrier to a subject in need thereof.

2 Claims, 6 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 71 amino acids
      (B) TYPE: amino acid
      (C) STRANDEDNESS: unknown
      (D) TOPOLOGY: unknown (ii) MOLECULE TYPE: peptide (xi) SEQUENCE DESCRIPTION: SEQ ID NO:1:

```
Cys Xaa Xaa Cys Xaa Xaa Asp Xaa Ala Xaa Gly Xaa Tyr Xaa Xaa Xaa
1               5                   10                  15

Xaa Cys Xaa Xaa Cys Lys Xaa Phe Phe Xaa Arg Xaa Xaa Xaa Xaa Xaa
            20                  25                  30
```

```
        Xaa Xaa Xaa Xaa Xaa Xaa Cys Xaa Xaa Xaa Xaa Xaa Xaa Xaa Xaa Cys
                    35                  40                  45

Xaa Xaa Xaa Lys Xaa Xaa Arg Xaa Xaa Cys Xaa Xaa Cys Arg Xaa Xaa
                    50                  55                  60

Lys Cys Xaa Xaa Xaa Gly Met
        65                  70

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (xi) SEQUENCE DESCRIPTION: SEQ ID NO:2:

TCAGGTCATG ACCTGA                                                                    16
```

METHOD FOR IN VIVO MODULATION OF NON-MALIGNANT SKIN-RELATED PROCESSES WITH 9-CIS-RETINOIC ACID

This application is a divisional of application Ser. No. 08/244,857, filed on Jun. 14, 1994, now pending, which is based on PCT/US92/11214, filed Dec. 18, 1992, which is a continuation-in-part of 07/809,980, filed Dec. 18, 1991, now abandoned.

FIELD OF THE INVENTION

The present invention relates to intracellular receptors, and ligands therefor. In a particular aspect, the present invention, relates to methods for modulating processes mediated by retinoid receptors.

BACKGROUND OF THE INVENTION

A central problem in eukaryotic molecular biology continues to be the elucidation of molecules and mechanisms that mediate specific gene regulation in response to exogenous inducers such as hormones or growth factors. As part of the scientific attack on this problem, a great deal of work has been done in efforts to identify exogenous inducers which are capable of mediating specific gene regulation.

Although much remains to be learned about the specifics of gene regulation, it is known that exogenous inducers modulate gene transcription by acting in concert with intracellular components, including intracellular receptors and discrete DNA sequences known as hormone response elements (HREs).

As additional members of the steroid/thyroid superfamily of receptors are identified, the search for exogenous inducers for such newly discovered receptors (i.e., naturally occurring (or synthetic) inducers) has become an important part of the effort to learn about the specifics of gene regulation.

The retinoid members of the steroid/thyroid superfamily of receptors, for example, are responsive to compounds referred to as retinoids, which include retinoic acid, retinol (vitamin A), and a series of natural and synthetic derivatives which have been found to exert profound effects on development and differentiation in a wide variety of systems.

The identification of compounds which interact with retinoid receptors, and thereby affect transcription of genes which are responsive to retinoic acid (or other metabolites of vitamin A), would be of significant value, e.g., for therapeutic applications.

Recently, a retinoic acid dependent transcription factor, referred to as RAR-alpha (retinoic acid receptor-alpha), has been identified. Subsequently, two additional RAR-related genes have been isolated; thus there are now at least three different RAR subtypes (alpha, beta and gamma) known to exist in mice and humans. These retinoic acid receptors (RARs) share homology with the superfamily of steroid hormone and thyroid hormone receptors and have been shown to regulate specific gene expression by a similar ligand-dependent mechanism [Umesono et al., Nature 336: 262 (1988)]. These RAR subtypes are expressed in distinct patterns throughout development and in the mature organism.

More recently, additional novel members of the steroid/thyroid superfamily of receptors have been identified, such as, for example, retinoid X receptor-alpha [RXR-α; see Mangelsdorf et al., in Nature 345: 224–229 (1990)], retinoid X receptor-beta [RXR-β; see Hamada et al., Proc. Natl. Acad. Sci. USA 86: 8289–8293 (1989)], and retinoid X receptor-gamma [RXR-γ; see Mangelsdorf et al., Genes and Development 6:329–344 (1992)]. While these novel receptors are responsive to retinoic acid, the primary exogenous inducer(s) for these receptors have not been identified.

Although both RAR and RXR respond to retinoic acid in vivo, the receptors differ in several important aspects. First, RAR and RXR are significantly divergent in primary structure (e.g., the ligand binding domains of RARα and RXRα have only 27% amino acid identity). These structural differences are reflected in different relative degrees of responsiveness of RAR and RXR to various vitamin A metabolites and synthetic retinoids. In addition, distinctly different patterns of tissue distribution are seen for RAR and RXR. In contrast to the RARS, which are not expressed at high levels in the visceral tissues, RXRα mRNA has been shown to be most abundant in the liver, kidney, lung, muscle and intestine. Finally, response elements have recently been identified in the cellular retinol binding protein type II (CRBPII) and apolipoprotein AI genes which confer responsiveness to RXR, but not RAR. Indeed, RAR has also been recently shown to repress RXR-mediated activation through the CRBPII RXR response element. These data, in conjunction with the observation that both RAR and RXR can activate through the RAR response element of the RARβ promoter, indicate that the two retinoic acid responsive pathways are not simply redundant, but instead manifest a complex interplay.

In view of the related, but clearly distinct nature of these receptors, the identification of ligands which are more selective for the retinoid X receptor than is retinoic acid would be of great value in selectively controlling processes mediated by one or both of these retinoid receptor types.

Other information helpful in the understanding and practice of the present invention can be found in commonly assigned, co-pending U.S. patent application Ser. Nos. 108,471, filed Oct. 20, 1987 (now issued as U.S. Pat. No. 5,071,773); 276,536, filed Nov. 30, 1988 (now issued as U.S. Pat. No. 4,981,784); 325,240, filed Mar. 17, 1989; 370,407, filed Jun. 22, 1989; and 438,757, filed Nov. 16, 1989, all of which are hereby incorporated herein by reference in their entirety.

BRIEF DESCRIPTION OF THE INVENTION

In accordance with the present invention, we have developed methods to modulate retinoid receptor mediated processes, employing high affinity, high specificity ligands for such receptors.

In a particular aspect of the present invention, there are provided ligands which are high affinity, high specificity ligands for retinoid receptors. Thus, in one aspect of the present invention, there are provided ligands which are more selective for the retinoid X receptor than is all-trans-retinoic acid. In another aspect of the present invention, we have discovered alternative ligands (other than all-trans-retinoic acid) which are capable of inducing retinoic acid receptor mediated processes.

In yet another aspect of the present invetion, we have developed methods for the preparation of such retinoid receptor ligands from readily available retinoid compounds.

Panel b is a similar comparison to that shown in panel a employing HPLC fraction 18 (instead of RA).

Figure 3A:
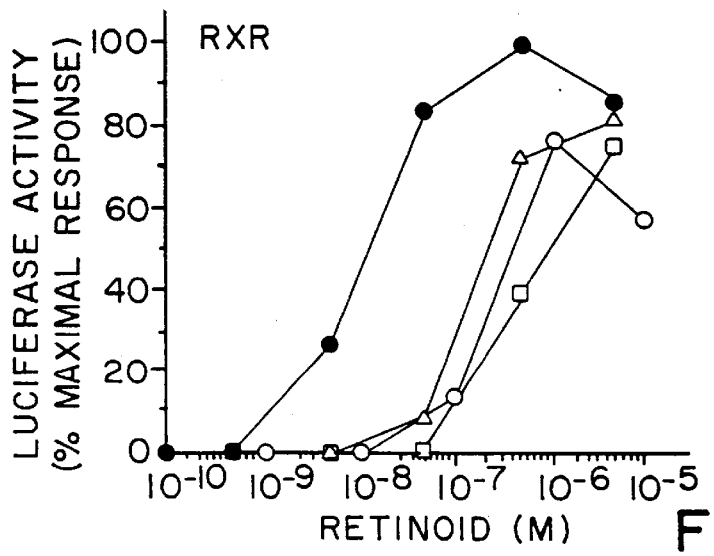

FIG. 3 presents several activation profiles for analysis of RXR-alpha or RAR-alpha activation by various retinoic acid isomers. Panel a. represents experiments done in insect S2 cells, while panels b. and c. represent experiments done in mammalian CV-1 cells. In the figure, closed circles are used to designate 9-cis-retinoic acid, open circles are used for all-trans-retinoic acid, open triangles are used for 13-cis-retinoic acid and open squares are used for 11-cis-retinoic acid.

FIG. 4 presents the results of saturation binding analysis of 9-cis-retinoic acid. Cell extracts were incubated with increasing concentrations of tritiated retinoid in the absence (total binding) or presence (non-specific binding) of 200-fold excess non-tritiated retinoid. Non-specific binding was subtracted from total binding and plotted as specific binding. The data shown in panel a represent specific [$^3$-H]-9-cis-retinoic acid binding to RXRα (closed circles) or mock (open circles) extracts; or specific [$^3$-H]-all-trans-retinoic acid binding to RXRα (open squares).

Panel b presents a Scatchard analysis, wherein specific 9-cis-retinoic acid binding to RXRα in (a) was transformed by Scatchard analysis and plotted. Linear regression yielded a Kd=11.7 nM (r=0.86).

Figure 5A:
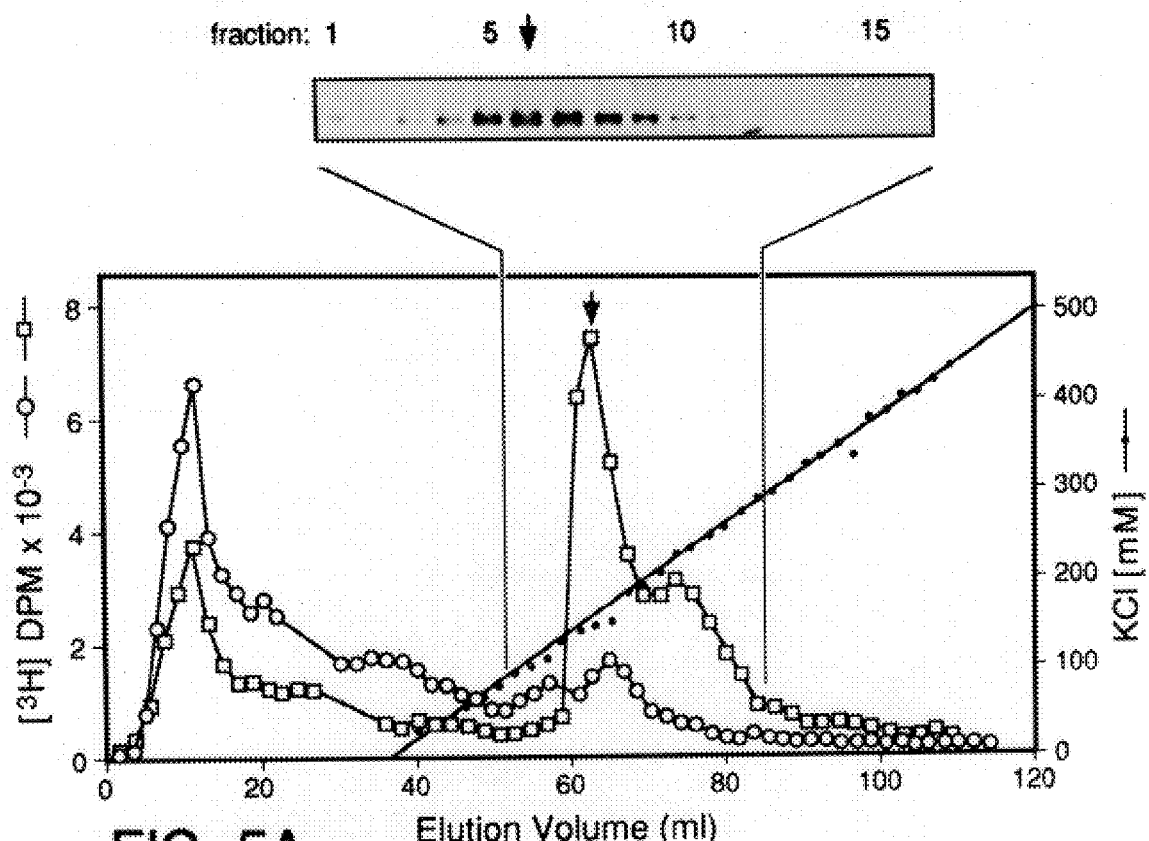

FIG. 5 presents a DNA-cellulose column profile of radio-labelled 9-cis-retinoic acid bound to baculovirus expressed RXR. In FIG. 5a, sample cell extracts containing RXRα protein were labelled with 10 nM [$^3$H]-9-cis-retinoic acid in the absence (open squares) or presence (open circles) of 200-fold excess non-radioactive 9-cis-retinoic acid, and then applied to the DNA-cellulose column. Fall-through radioactivity was monitored until a consistent baseline was established. DNA-binding components were then eluted with a linear salt gradient. The peak radioactive fractions (labelled 1–15) were then subjected to immunoblot analysis using an hRXRα-specific antisera. The peak radioactive fraction (indicated by an arrow) co-migrated exactly with the peak amount of RXRα-specific protein.

Figure 5B:
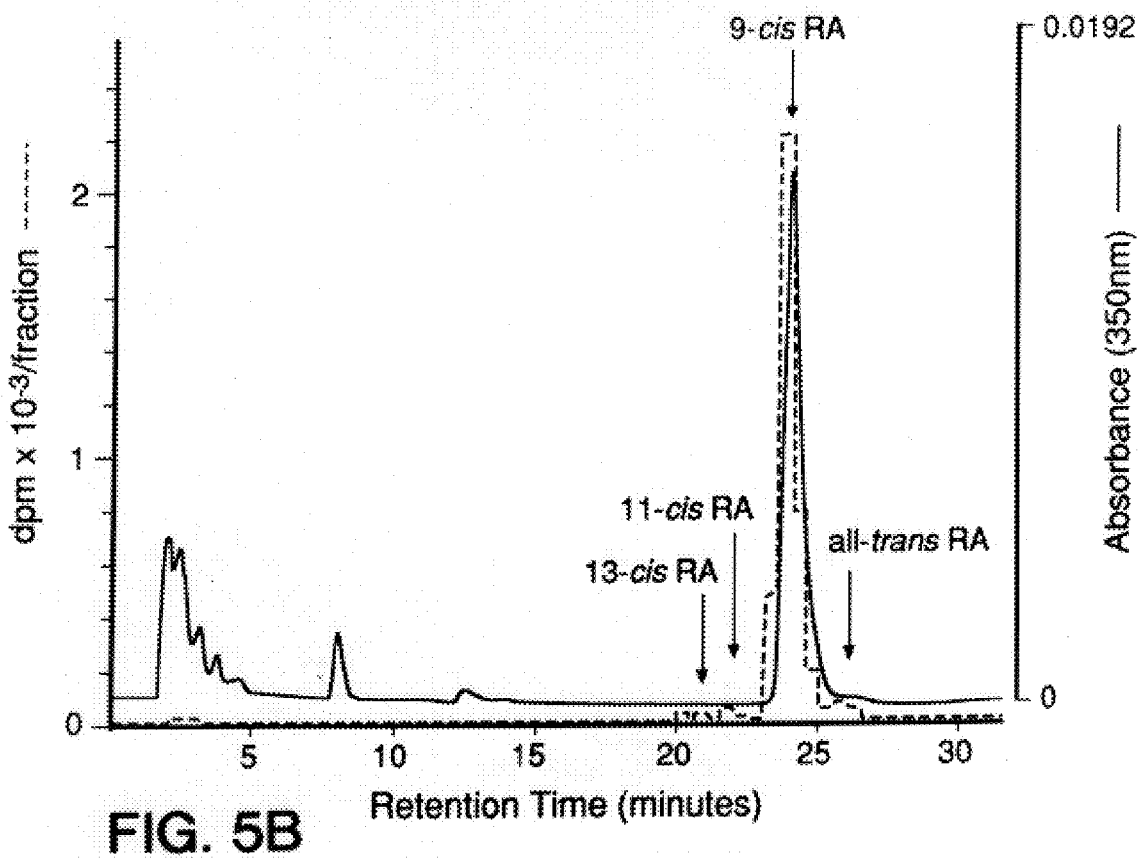

In FIG. 5b, the peak radioactive fraction of the DNA-cellulose column is shown to contain 9-cis-retinoic acid. The peak fraction (arrow in (a)) was extracted and analyzed on a $C_{18}$ column developed with mobile phase G. As shown, 0.95% of the extracted radioactivity co-elutes with authentic 9-cis-retinoic acid (absorbance peak).

Figure 6:
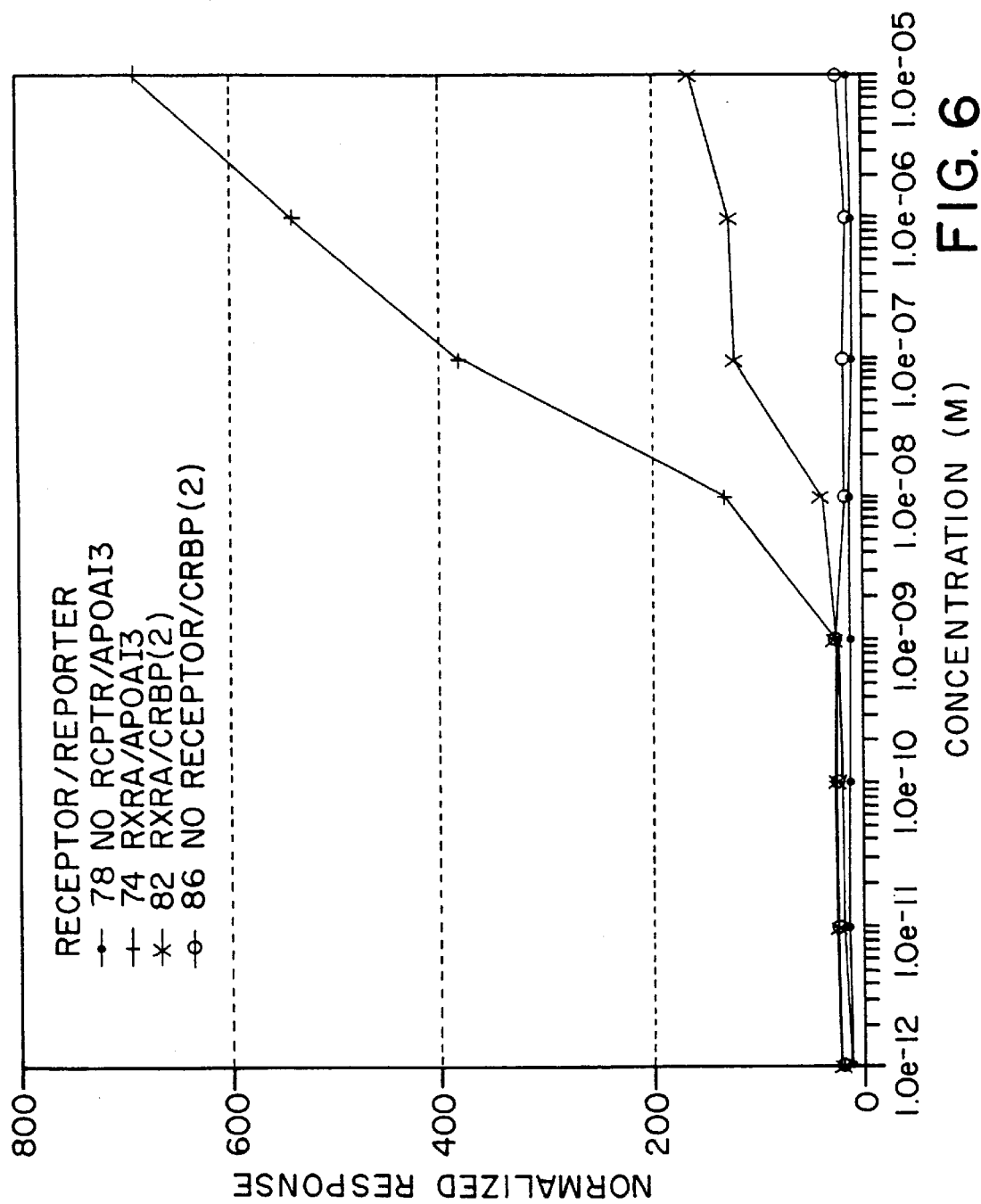

FIG. 6 is a comparison of the transactivation profile for RXR-alpha in the presence of 9-cis-retinoic acid employing a luciferase reporter containing the retinoid response element derived from either the apolipoprotein A1 gene (APOA13) or cellular retinol binding protein, type II (CRBPII).

DETAILED DESCRIPTION OF THE INVENTION

In accordance with the present invention, there is provided a method for modulating process(es) mediated by retinoid receptors, said method comprising conducting said process(es) in the presence of at least one compound of the structure:

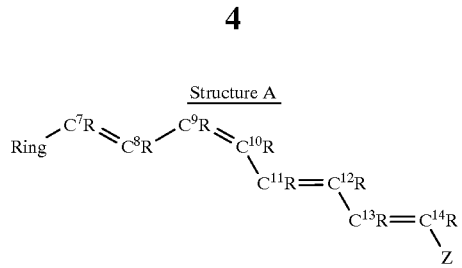

Structure A wherein
unsaturation between carbon atoms $C^9$ and $C^{10}$ has a cis configuration, and one or both sites of unsaturation between carbon atoms $C^{11}$ through $C^{14}$ optionally have a cis configuration;

"Ring" is a cyclic moiety, optionally having one or more substituents thereon;

Z is selected from carboxyl (—COOH), carboxaldehyde (—COH), hydroxyalkyl [—(CR'$_2$)$_n$—OH, wherein each R' is independently selected from hydrogen or a lower alkyl and n falls in the range of 1 up to about 4], thioalkyl [—(CR'$_2$)$_n$—SH, wherein R' and n are as defined above], hydroxyalkyl phosphate [—(CR'$_2$)$_n$—OP(OM)$_3$, wherein R' and n are as defined above and M is hydrogen, lower alkyl, or a cationic species such as Na$^+$, Li$^+$, K$^+$, and the like], alkyl ether of a hydroxyalkyl group [—(CR'$_2$)$_n$—OR', wherein R' and n are as defined above], alkyl thioether of a thioalkyl group [—(CR'$_2$)$_n$—SR', wherein R' and n are as defined above], esters of hydroxyalkyl groups [—(CR'$_2$)$_n$—O—CO—R', wherein R' and n are as defined above], thioesters of hydroxyalkyl group [—(CR'$_2$)$_n$—O—CS—R', wherein R' and n are as defined above], esters of thioalkyl groups [—(CR'$_2$)$_n$—S—CO—R', wherein R' and n are as defined above], thioesters of thioalkyl groups [—(CR'$_2$)$_n$—S—CS—R', wherein R' and n are as defined above], aminoalkyl [—(CR'$_2$)$_n$—NR'$_2$, wherein R' and n are as defined above], N-acyl aminoalkyl [—(CR'$_2$)$_n$—NR'—CO—R", wherein R' and n are as defined above and R" is a lower alkyl or benzyl], carbamate [—(CR'$_2$)$_n$—NR'—CO—OR' or —(CR'$_2$)$_n$—O—CO—NR'$_2$, wherein R' and n are as defined above], and the like; and each R is independently selected from H, halogen, alkyl, aryl, hydroxy, thiol, alkoxy, thioalkoxy, amino, or any of the Z substituents, and the like; or any two or more of the R groups can be linked to one another to form one or more ring structures.

Exemplary R groups in the latter situation are selected from alkylene, oxyalkylene, thioalkylene, and the like.

As employed herein, the term "modulate" refers to the ability of a ligand for a member of the steroid/thyroid superfamily to induce expression of gene(s) maintained under hormone expression control, or to repress expression of gene(s) maintained under such control.

As employed herein, the phrase "processes mediated by retinoid receptors" refers to biological, physiological, endocrinological, and other bodily processes which are mediated by receptor or receptor combinations which are responsive to natural or synthetic retinoids, or natural or synthetic compounds as defined herein (referred to herein as "rexoids" because of the ability of many of the compounds described herein to selectively activate retinoid X receptors). Modulation of such processes can be accomplished in vitro or in vivo. In vivo modulation can be carried out in a wide range of subjects, such as, for example, humans, rodents, sheep, pigs, cows, and the like.

Exemplary receptors which are responsive to retinoids, and natural or synthetic compounds as defined herein (i.e., "rexoids"), include retinoic acid receptor-alpha, retinoic acid receptor-beta, retinoic acid receptor-gamma, and splicing variants encoded by the genes for such receptors; retinoid X receptor-alpha, retinoid X receptor-beta, retinoid X receptor-gamma, and splicing variants encoded by the genes for such receptors; as well as various combinations thereof (i.e., homodimers, homotrimers, heterodimers, heterotrimers, and the like), including combinations of such receptors with other members of the steroid/thyroid superfamily of receptors with which the retinoid receptors may interact by forming heterodimers, heterotrimers, and higher heteromultimers. For example, the retinoic acid receptor-alpha may form a heterodimer with retinoid X receptor-alpha, the retinoic acid receptor-beta may form a heterodimer with retinoid X receptor-alpha, retinoic acid receptor-gamma may form a heterodimer with retinoid X receptor-alpha, retinoid X receptor-alpha may form a heterodimer with thyroid receptor, retinoid X receptor-beta may form a heterodimer with vitamin D receptor, retinoid X receptor-gamma may form a heterodimer with retinoic acid receptor-alpha, and the like.

As employed herein, the phrase "members of the steroid/thyroid superfamily of receptors" (also known as "nuclear receptors" or "intracellular receptors") refers to hormone binding proteins that operate as ligand-dependent transcription factors, including identified members of the steroid/thyroid superfamily of receptors for which specific ligands have not yet been identified (referred to hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66–68 amino acid residues, and possessing about 20 invariant amino acid residues, including nine cysteines.

A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153). The highly conserved amino acids of the DNA-binding domain of members of the superfamily are as follows:

wherein X designates non-conserved amino acids within the DNA-binding domain; the amino acid residues denoted with an asterisk are residues that are almost universally conserved, but for which variations have been found in some identified hormone receptors; and the residues enclosed in parenthesis are optional residues (thus, the DNA-binding domain is a minimum of 66 amino acids in length, but can contain several additional residues).

Exemplary members of the steroid/thyroid superfamily of receptors include steroid receptors such as glucocorticoid receptor, mineralocorticoid receptor, progesterone receptor, androgen receptor, vitamin $D_3$ receptor, and the like; plus retinoid receptors, such as RARα, RARβ, RARγ, and the like, plus RXRα, RXRβ, RXRγ, and the like; thyroid receptors, such as TRα, TRβ, and the like; as well as other gene products which, by their structure and properties, are considered to be members of the superfamily, as defined hereinabove. Examples of orphan receptors include HNF4 [see, for example, Sladek et al., in Genes & Development 4: 2353–2365 (1990)], the COUP family of receptors [see, for example, Miyajima et al., in Nucleic Acids Research 16: 11057–11074 (1988), Wang et al., in Nature 340: 163–166 (1989)], COUP-like receptors and COUP homologs, such as those described by Mlodzik et al., in Cell 60: 211–224 (1990) and Ladias et al., in Science 251: 561–565 (1991), the ultraspiracle receptor [see, for example, Oro et al., in Nature 347: 298–301 (1990)], and the like.

Processes capable of being modulated by retinoid receptors, in accordance with the present invention, include in vitro cellular differentiation and proliferation, in vitro proliferation of melanoma cell lines, in vitro differentiation of mouse teratocarcinoma cells (F9 cells), in vitro differentiation of human epidermal keratinocytes, limb morphogenesis, regulation of cellular retinol binding protein (CRBP), and the like. As readily recognized by those of skill in the art, the availability of ligands for the retinoid X receptor makes it possible, for the first time, to carry out assays for the identification of antagonists for said receptor.

Processes capable of being modulated by retinoid receptors, in accordance with the present invention, also include the in vivo modulation of lipid metabolism, in vivo modulation of skin-related processes (e.g., acne, aging, wrinkling, skin cancer, and the like), in vivo modulation of malignant cell development, such as occurs, for example, in acute promyelocytic leukemia, testicular cancer, lung cancer, and the like. The ability of compounds of the invention to modulate such processes is evidenced in a number of ways. See, for example, FIG. 6 where the ability of RXR-alpha, in the presence of ligand therefor (e.g., 9-cis-retinoic acid) is shown to exert a strong effect on the

```
Cys - X - X - Cys - X - X - Asp* - X -    (SEQ ID NO 1);

Ala* - X - Gly* - X - Tyr* - X - X -

X - X - Cys - X - X - Cys - Lys* -

X - Phe - Phe - X - Arg* - X - X - X -

X - X - X - X - X - X - (X - X -) Cys -

X - X - X - X - X - (X - X - X - ) Cys -

X - X - X - Lys - X - X - Arg - X - X -

Cys - X - X - Cys - Arg* - X - X -

Lys* - Cys - X - X - X - Gly* - Met
``` expression of genes under the control of regulatory elements of apolipoprotein AI. Similarly, studies with model systems for a variety of disease states (e.g., differentiation of HL60 cells as a model for acute promyelocytic leukemia, proliferation of melanoma cell lines as a model for skin cancer, differentiation of keratinocytes as a model for non-malignant skin disorders, and the like), as set forth in the Examples, demonstrate the ability of retinoid receptors, in the presence of ligand therefor, e.g., 9-cis-retinoic acid, to exert a strong effect on such disease states. Such in vivo applications of the invention process may allow the modulation of various biological processes with reduced occurrence of undesirable side effects, and the like.

In vivo applications of the invention process(es) (and compositions) can be employed with a wide range of subjects, such as, for example, humans, rodents, sheep, pigs, cows, and the like.

As employed herein, the term "alkyl" refers to "lower alkyl", i.e., alkyl moieties having in the range of 1 up to about 4 carbon atoms, i.e., methyl groups, ethyl groups, propyl groups, isopropyl groups, normal-butyl groups, isobutyl groups, sec-butyl groups, tert-butyl groups, and the like.

Cyclic moieties contemplated as part of the compounds employed in the practice of the present invention include 5-, 6-, and 7-membered carbocyclic, heterocyclic aromatic or heteroaromatic rings. Included in this definition, for example, are optionally substituted saturated, mono-unsaturated or polyunsaturated carbocyclic species, such as, for example, cyclopentane, cyclopentene, cyclohexane, cyclohex-2-ene, cyclohex-3-ene, cyclohex-4-ene, and cyclohex-5-ene isomers, and 2,4-, 2,5-, and 3,5-cyclohexadiene variants thereof. Examples of heterocyclic species contemplated as part of the compounds employed in the practice of the present invention include dihydrofuran, tetrahydrofuran, dihydrothiophene, tetrahydrothiophene, dihydropyran, tetrahydropyran, dihydrothiopyran, tetrahydrothiopyran, piperidine, pyrrolidine, and the like, as well as derivatives thereof. Examples of aromatic or heteroaromatic species contemplated as part of the rexoid compounds of the present invention include phenyl, tolyl, xylyl, mesityl, benzyl, pyridyl, thiophenyl, furanyl, and the like, as well as derivatives thereof.

Preferred cyclic moieties are typically geminally di-substituted, mono-unsaturated species. Presently preferred geminally di-substituted, mono-unsaturated cyclic moieties are the 1,1,5-trisubstituted cyclohex-5-ene structure of naturally occurring retinoic acid (i.e., the ring structure of β-ionone; the position of the substituents on the ring are designated employing the traditional retinoic acid numbering convention for the ring structure of β-ionone), as well as the 1,1,4,5-tri-substituted cyclohex-5-ene structure provided by hydroxy- or keto-substituted derivatives of the traditional β-ionone structure.

Compounds contemplated for use in the practice of the present invention include compounds having the structure:

Structure A

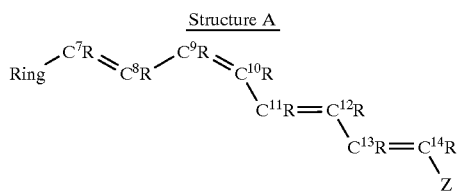

wherein:

unsaturation between carbon atoms $C^9$ and $C^{10}$ has a cis configuration, and one or both sites of unsaturation between carbon atoms $C^{11}$ through $C^{14}$ optionally have a cis configuration;

"Ring" is a cyclic moiety;

Z is selected from carboxyl, carboxaldehyde, hydroxyalkyl, thioalkyl, hydroxyalkyl phosphate, alkyl ether of a hydroxyalkyl group, alkyl thioether of a thioalkyl group, esters of hydroxyalkyl groups, thioesters of hydroxyalkyl group, esters of thioalkyl groups, thioesters of thioalkyl groups, aminoalkyl, N-acyl aminoalkyl, carbamate, and the like; and R on each of $C^7$, $C^8$, $C^9$, $C^{10}$, $C^{11}$, $C^{12}$, $C^{13}$, or $C^{14}$ is independently selected from H, halogen, alkyl, aryl, hydroxy, thiol, alkoxy, thioalkoxy, amino, or any of the Z substituents; or any two or more of the R groups can be linked to one another to form one or more ring structures.

Presently preferred compounds which are contemplated by the above generic structure include 9-cis-retinoic acid, as well as novel derivatives thereof such as 9-phenyl-9-cis-retinoic acid, 4-hydroxy-9-cis-retinoic acid, 4-keto-9-cis-retinoic acid, and the like.

In another preferred embodiment of the present invention, the substituents on $C^9$ and $C^{13}$ are methyl; in yet another preferred embodiment, the substituents on two or more of the side chain carbons (i.e., $C^7$, $C^8$, $C^9$, $C^{10}$, $C^{11}$, $C^{12}$, $C^{13}$, or $C^{14}$) can be linked together to form a ring structure. For example, the substituents on $C^8$ and $C^{11}$ can be linked together to form a structure having a constrained 9-cis double bond (i.e., a 9-cis locked rexoid derivative), as follows:

Structure I

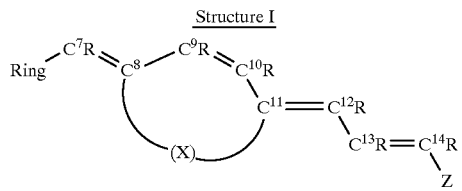

wherein:

X is $-[(CR_2)_x-X'-(CR_2)_y]-$,

X' is selected from $-O-$, carbonyl (>CO), $-S-$, $-S(O)-$, $-S(O)_2-$, thiocarbonyl (>CS), $-NR''-$, or $-CR_2-$, R, Ring and Z are as defined above, R" is hydrogen, alkyl, hydroxy, thiol, or alkoxy acyl ($-CO-O-$alkyl);

x is 0, 1 or 2, y is 0, 1, or 2, and $x+y \leq 2$.

Such compounds include cyclopentene derivatives, cyclohexene derivatives, cycloheptene derivatives, dihydrofuran derivatives, dihydropyrrole derivatives, and the like, wherein the cyclic structure linking $C^8$ and $C^{11}$ serves to prevent isomerization of the cis double bond between $C^9$ and $C^{10}$.

Especially preferred derivatives of structure I are those where Z is a carboxyl group, and Ring is a β-ionone-like species having the structure:

β-ionone ring structure

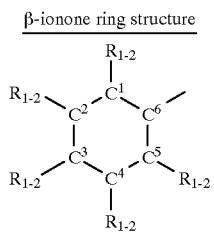

wherein each R is independently defined as provided above;

any one of $C^2$, $C^3$, or $C^4$ can be replaced with —O—, carbonyl (>CO), —S—, —S(O)—, —S(O)$_2$—, thiocarbonyl (>CS), or —NR″—; wherein R″ is as defined above; and said cyclic moiety exists as the saturated, 2-ene, 3-ene, 4-ene, or 5-ene mono-unsaturated isomer; the 2,4-, 2,5-, or 3,5-diene derivative thereof; or an aromatic derivative thereof.

Especially preferred species for use in the practice of the present invention are derivatives of structure I where Z is a carboxyl group, and Ring is a 1,1,5-trisubstituted cyclohex-5-ene structure or a 1,1,4,5-tetrasubstituted cyclohex-5-ene structure.

Similarly, the substituents on $C^{10}$ and $C^{13}$ can be linked together to form a structure having a constrained 9, 11-di-cis configuration (i.e., a 9-cis locked rexoid derivative), as follows:

Structure II

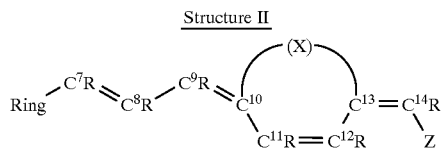

wherein:

X, X', R, R″, Z, Ring, x and y are as defined above.

Such compounds include cyclopentene derivatives, cyclohexene derivatives, cycloheptene derivatives, dihydrofuran derivatives, dihydropyrrole derivatives, and the like, wherein the cyclic structure linking $C^{10}$ and $C^{13}$ serves to hinder isomerization of the cis double bond between $C^9$ and $C^{10}$, and prevent isomerization of the cis double bond between $C^{11}$ and $C^{12}$.

Especially preferred derivatives of Structure II are those where Z is a carboxyl group, and the Ring is a 1,1,5-trisubstituted cyclohex-5-ene structure or a 1,1,4,5-tetrasubstituted cyclohex-5-ene structure.

Similarly, at least two of the substituents on $C^8$ $C^{11}$, and/or $C^{14}$ can be linked together to form a structure having a constrained 9, 13-di-cis configuration (i.e., a 9-cis locked rexoid derivative), shown below as Structure III:

Structure III

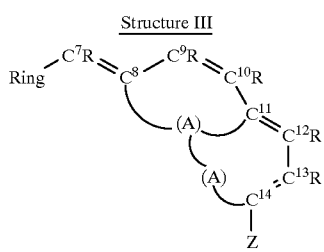

wherein:

one A is X and the other A is X', and

X, X', R, R″, Z, Ring, x and y are as defined above. Those of skill in the art recognize that the junction between the two bridging groups (A) can only occur through an atom with a valence of three or four (i.e., through carbon or nitrogen), so as to accomodate the bonds required to link the fused rings together.

Similarly, at least two of the substituents on $C^8$, $C^{11}$, and/or $C^{14}$ can be linked together, and further linked to $C^5$ of Ring, or to a substituent on $C^5$ to form a structure having a constrained 9, 13-di-cis configuration (i.e., a 9-cis locked rexoid derivative), shown below as Structure IV:

Structure IV

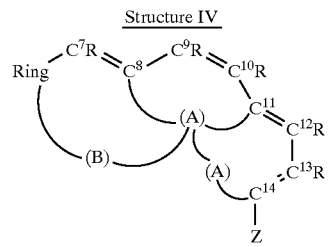

wherein:

one A is X and the other A is X',

B is X', and

X, X', R, R″, Z, Ring, x and y are as defined above. As noted above with respect to Structure III, those of skill in the art recognize that the junction(s) between the bridging groups (A) and (B) can only occur through an atom with a valence of three or four (i.e., through carbon or nitrogen), so as to accomodate the bonds required to link the fused rings together.

Such compounds include cyclopentene derivatives, cyclohexene derivatives, cycloheptene derivatives, dihydrofuran derivatives, dihydropyrrole derivatives, and the like, wherein the cyclic structures linking $C^8$, $C^{11}$ and/or $C^{13}$ serves to prevent isomerization of the cis double bonds at carbon 9 and carbon 13.

Especially preferred derivatives of Structures III and IV are those where Z is a carboxyl group, and Ring is a 1,1,5-trisubstituted cyclohex-5-ene structure or a 1,1,4,5-tetrasubstituted cyclohex-5-ene structure.

Similarly, the substituents on $C^{10}$ and $C^{11}$ can be linked together to form a structure having a constrained 9-cis double bond (i.e., a 9-cis locked rexoid derivative), as follows:

Structure V

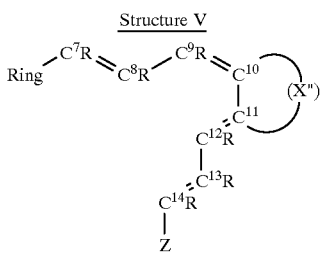

wherein:

X" is —[(CR$_2$)$_a$—X'—(CR$_2$)$_b$]—,

X', R, R", Ring and Z are as defined above, a is 0, 1, 2, 3 or 4, b is 0, 1, 2, 3, or 4, and a+b is $\geq 2$, but $\leq 4$.

Such compounds include cyclopentene derivatives, cyclohexene derivatives, cycloheptene derivatives, dihydrofuran derivatives, dihydropyrrole derivatives, and the like, wherein the cyclic structure linking $C^{10}$ and $C^{11}$ serves to prevent isomerization of the cis double bond between $C^9$ and $C^{10}$.

Especially preferred derivatives of Structure V are those where Z is a carboxyl group, and Ring is a 1,1,5-trisubstituted cyclohex-5-ene structure or a 1,1,4,5-tetrasubstituted cyclohex-5-ene structure.

Similarly, the substituents on $C^7$ and $C^9$ can be linked together, and the substituents on $C^{10}$ and $C^{12}$ can be linked together to form a structure having a constrained 9-cis double bond (i.e., a 9-cis locked rexoid derivative), as follows:

Structure VI

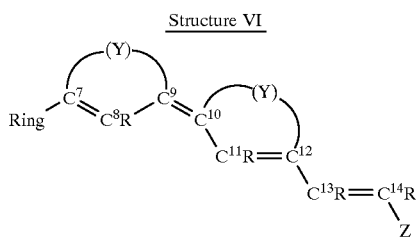

wherein:

Y is —[(CR$_2$)$_c$—X'—(CR$_2$)$_d$]—,

X', R, R", Ring and Z are as defined above, c is 0, 1, 2 or 3, d is 0, 1, 2 or 3, and c+d $\geq$ 1, but $\leq$ 3.

Such compounds include cyclopentene derivatives, cyclohexene derivatives, cycloheptene derivatives, dihydrofuran derivatives, dihydropyrrole derivatives, and the like, wherein the cyclic structures linking $C^7$ and $C^9$, and $C^{10}$ and $C^{12}$ serve to prevent isomerization of the cis double bond between $C^9$ and $C^{10}$.

Especially preferred derivatives of Structure VI are those where Z is a carboxyl group, and Ring is a 1,1,5-trisubstituted cyclohex-5-ene structure or a 1,1,4,5-tetrasubstituted cyclohex-5-ene structure.

Similarly, the substituents on $C^9$ and $C^{10}$ can be linked together to form a structure having a constrained C-9 double bond (i.e., a 9-cis locked rexoid derivative), as follows:

Structure VII

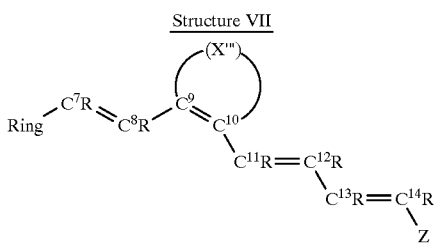

wherein:

X'" is X" or an unsaturated linking group having the structure:

—[Q=CR—J]—, wherein Q is —N= or —CR=, an J is —CR=CR—, —N=CR—, —CR=N—, —O—, —S—, or —NR"—, thereby incorporating $C^9$ and $C^{10}$ of the rexoid compound into an aromatic (or pseudo-aromatic) ring, and X', X", R, R", Ring, Z, a and b are as defined above.

Such compounds include cyclohexene derivatives, cycloheptene derivatives, benzene derivatives, pyridine derivatives, furan derivatives, thiophene derivatives, pyrrole derivatives, oxazole derivatives, thiazole derivatives, imidazole derivatives, pyrazole derivatives, and the like, wherein the cyclic structure linking $C^9$ and $C^{10}$ serves to prevent isomerization of the $C^9$–$C^{10}$ double bond; however, rotation about the 8–9 and/or 10–11 single bonds can still occur.

Especially preferred derivatives of Structure VII are those where Z is a carboxyl group, and Ring is a 1,1,5-trisubstituted cyclohex-5-ene structure or a 1,1,4,5-tetrasubstituted cyclohex-5-ene structure.

In addition to the structures set forth above, those of skill in the art can readily identify additional means to constrain the basic cis-configuration containing rexoid compounds employed in the practice of the present invention.

In accordance with a preferred embodiment of the present invention, the cyclic moiety has the β-ionone structure set forth above. Especially preferred are the 1,1,5-trisubstituted cyclohex-5-ene structure (characteristic of β-ionone) as well as the closely related 1,1,4,5-tetrasubstituted cyclohex-5-ene structure from which many rexoid compounds according to the present invention can be prepared.

In accordance with a particularly preferred embodiment of the present invention, the compounds employed in the invention process are selected from 9-cis-retinoic acid and derivatives thereof as contemplated by Structure A set forth above, as well as 9-cis-locked derivatives of retinoic acid as set forth in Structures I–VII above. Examples of specific compounds contemplated for use in the practice of the present invention are compounds wherein Z is carboxy, Ring is the 1,1,5-trisubstituted cyclohex-5-ene structure charateristic of β-ionone (or the closely related 1,1,4,5-tetrasubstituted cyclohex-5-ene), and having a side chain structure(s) as described above for Structures I–VII.

"Rexoid" derivatives as described above can be prepared employing a variety of synthetic methods, which are readily available (and well known) to those of skill in the art. See, for example, the methods described in *Chemistry and Biology of Synthetic Retinoids*, Dawson and Okamura, eds., CRC Press, Inc. (1990), especially Chapter 4, by Ito (found at pages 78–97), and Chapter 9, by de Lera et al. (found at pages 202–227) can readily be adapted for the preparation of the compounds described herein. The contents of this publication are hereby incorporated by reference herein. See also Asato et al., J. Am. Chem. Soc. 108: 5032 (1986); Sheves et al., J. Am. Chem. Soc. 108: 6440 (1986); Akita et al., J. Am. Chem. Soc. 102: 6370 (1980); Derguini and Nakanishi, Photobiochem. and Photobiophys. 13: 259 (1986), the entire contents of each of which is hereby incorporated by reference herein.

In accordance with another embodiment of the present invention, there is provided a method for modulating processes mediated by retinoid receptors, said method comprising conducting said process in the presence of:

(a) at least one compound of the structure:

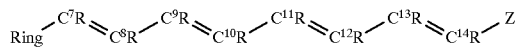

wherein:
each site of unsaturation in the side chain comprising carbon atoms $C^7$ through $C^{14}$ has a trans configuration;
"Ring", Z, and R are as previously described, and
(b) a cis/trans isomerase capable of converting at least the 9-double bond from the trans configuration to the cis-configuration.

As employed herein, the term "cis/trans isomerase" refers to enzymes which promote a change of geometrical configuration at a double bond. Examples of such enzymes include maleate isomerase, maleylacetoacetate isomerase, retinal isomerase, maleylpyruvate isomerase, linoleate isomerase, furylfuramide isomerase, and the like.

In accordance with yet another embodiment of the present invention, there is provided a method to produce compound(s) of the structure:

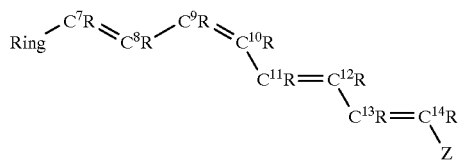

wherein:
unsaturation between carbon atoms $C^9$ and $C^{10}$ has a cis configuration, and one or both sites of unsaturation between carbon atoms $C^{11}$ through $C^{14}$ optionally have a cis configuration;
"Ring" is a cyclic moiety;
Z is selected from carboxyl, carboxaldehyde, hydroxyalkyl, thioalkyl, hydroxyalkyl phosphate, alkyl ether of a hydroxyalkyl group, alkyl thioether of a thioalkyl group, esters of hydroxyalkyl groups, thioesters of hydroxyalkyl group, esters of thioalkyl groups, thioesters of thioalkyl groups, aminoalkyl, N-acyl aminoalkyl, carbamate, and the like; and
each R is independently selected from H, halogen, alkyl, aryl, hydroxy, thiol, alkoxy, thioalkoxy, amino, or any of the Z substituents;
from the corresponding all-trans configuration material, said method comprising contacting said all-trans configuration material with a cis/trans isomerase under isomerization conditions.

In accordance with still another embodiment of the present invention, there are provided novel compositions comprising compound(s) of Structure A (excluding previously identified compounds such as retinoic acid as well as constrained compounds selected from Structures I–VII, as set forth above. Examples of such compounds include 9-phenyl-9-cis-retinoic acid, 4-hydroxy-9-cis-retinoic acid, 4-keto-9-cis-retinoic acid, and the like. Presently preferred compounds are those wherein Z is carboxyl and Ring is a 1,1,5-trisubstituted cyclohex-5-ene structure or a 1,1,4,5-tetrasubstituted cyclohex-5-ene structure.

The invention compounds can be employed for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effect activation of retinoid receptor(s). Such a concentration typically falls in the range of about 10 nM up to 2 $\mu$M; with concentrations in the range of about 100 nM up to 200 nM being preferred.

In accordance with a particular embodiment of the present invention, compositions comprising at least one 9-cis-retinoic acid-like compound (as described above), and a pharmaceutically acceptable carrier are contemplated. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of terile water, or some other sterile injectable medium mmediately before use.

The invention will now be described in greater etail by reference to the following non-limiting examples.

EXAMPLES

Example 1

Identification of Compound(s) that Activate RXR

In order to acertain if retinoic acid can be converted to a product that binds directly to RXR, thereby resulting in modulation of transcription, a strategy was developed to identify retinoic acid metabolites that might modulate the transcriptional properties of RXR. The identification of any such active metabolite would allow one to further determine whether this metabolite was capable of directly binding to the receptor protein.

Accordingly, the Drosophila melanogaster Schneider cell line (S2) was incubated with or without all-trans-retinoic acid (RA) for a period of 24 hours. Prior to the addition of retinoic acid, *Drosophila melanogaster* Schneider cell line (S2) cells were grown in Schneider Drosophila medium (GIBCO) supplemented with penicillin, streptomycin and 12% heat inactivated FCS (Irvine Scientific). One hundred tissue culture flasks (75 cm$^2$) were set up with 10$^7$ cells and 12 ml of medium/flask. Twenty four hours later, either all-trans-retinoic acid (or ethanol solvent control) was added to each flask to a final concentration of 5×10$^{-6}$M in reduced light conditions. Cells were harvested 24 hours later by centrifugation for 5 minutes at 800 g. Cells were washed twice with PBS and the resultant pellets were frozen at −80° C. until extraction.

In parallel, CV-1 cells were set up on 64 tissue culture dishes (150 mm) at 2×10$^6$ cells and 25 ml of medium/dish. Cells were treated with retinoic acid and harvested as with the S2 cells except that the CV-1 cells (which are adherent) were washed in their dishes with PBS nd scraped with a rubber policeman prior to centrifugation and freezing.

Following incubation, the cell pellets were collected, organically extracted and chromatographically fractionated by HPLC. The various HPLC fractions were assayed for their ability to produce a ligand dependent increase in transcriptional activity mediated by RXR. This assay system involves transfecting cells with the cDNA for the RXR receptor and a luciferase reporter molecule which is under control of a promoter containing a RXR response element (RXRE) [see Mangelsdorf et al., Cell 66:555 (1991)]. The addition of a ligand capable of activating RXR results in an increase in luciferase activity.

Schneider cells, CV-1 cells and mouse tissues were extracted as described by C. Thaller and G. Eichele in Nature Vol. 327:625 (1987). Mouse tissue was used to determine if any RXR ligand is present in vivo. In the case of tissue extractions, 2.10$^5$ dpm internal standard [11,12-$^3$H]-all-trans-retinoic acid (New England Nuclear) or 9-cis-retinoic acid (generated by isomerization with light) were added to the homogenate. Extracts were fractionated on a Waters Novapak 300 mm C$_{18}$ analytical column at a flow rate of 1 ml min$^{-1}$. The mobile phase (G) was a 1:1 mixture of:

A [CH$_3$CN/CH$_3$OH/2% aqueous CH$_3$COOH (3:1:1)] and
E [CH$_3$CN/CH$_3$OH/2% aqueous CH$_3$COOH (11:3:10)].

Other mobile phases used have the following compositions:

C: CH$_3$CN/CH$_3$OH/H$_2$O/CH$_3$COOH (80:10:10:1),
H: mix CH$_3$OH/10 mM ammonium acetate (9:1) with equal volume of CH$_3$OH/10 mM ammonium acetate (3:1).

Methyl esters of retinoic acid isomers and/or metabolites contained in the HPLC fractions were generated as described in Wedden et al. [Meth. Enzymol. 190:201 (1990)]. Reference standards used were from Aldrich, Sigma or kindly provided by Hoffmann-LaRoche. Authentic 9-cis-retinol, 9-cis-retinoic acid and 9-cis-methylretinoate were either synthesized from 9-cis-retinal [see E. J. Corey et al., J. Am. Chem. Soc. 90:5616 (1968); C. D. B. Bridges & R. A. Alvares (Meth. Enzymol. 81:463 (1982)] or generated by photoisomerization of the all-trans isomer followed by fractionation of the resulting isomers by HPLC.

Photoisomerization of all-trans-retinoic acid is carried out employing standard isomerization techniques which are well known to those of skill in the art. For example, retinoic acid can be dissolved in a polar organic solvent such as ethanol, placed in a quartz cuvette, and irradiated with a variety of wavelengths of light (such as fluorescent light). Temperature at which irradiation is carried out is not critical; accordingly, irradiation can be carried out at room temperature. Irradiation time is also not critical; typical irradiation times are in the range of about 0.5–2 hours.

The various HPLC fractions were diluted 1:100 and assayed for their ability to modulate the transcriptional properties of RXR.

Cotransfection Assay in CV-1 Cells

A monkey kidney cell line, CV-1, was used in the cis-trans assay. Cells were transfected with two DNA transfection vectors. The trans-vector allowed efficient production of retinoid receptor (e.g., RAR or RXR) in these cells, which do not normally express these receptors. The cis-vector contains an easily assayable gene, in this case the firefly luciferase, coupled to a retinoid-responsive promoter. Addition of retinoic acid or an appropriate synthetic retinoid results in the formation of a retinoid-receptor complex that activates the luciferase gene, causing light to be emitted from cell extracts. The level of luciferase activity is directly proportional to the effectiveness of the retinoid-receptor complex in activating gene expression. This sensitive and reproducible cotransfection approach permits the identification of retinoids that interact with the different receptor isoforms.

Cells were cultured in DMEM supplemented with 10% charcoal resin-stripped fetal bovine serum, and experiments were conducted in 96-well plates. The plasmids were transiently transfected by the calcium phosphate method [Umesono and Evans, Cell 57:1139–1146 (1989); Berger et al., J. Steroid Biochem. Molec. Biol. 41:733–738 (1992)] by using 10 ng of a pRS (Rous sarcoma virus promoter) receptor-expression plasmid vector, 50 ng of the reporter luciferase (LUC) plasmid, 50 ng of pRSβ-GAL (β-galactosidase) as an internal control, and 90 ng of carrier plasmid PGEM. Cells were transfected for 6 hours and then washed to remove the precipitate. The cells were then incubated for 36 hours with or without retinoid. After the transfection, all subsequent steps were performed on a Beckman Biomek Automated Workstation. Cell extracts were prepared as described by Berger et al. supra, then assayed for luciferase and β-galactosidase activities. All determinations were performed in triplicate in two independent experiments and were normalized for transfection efficiency by using β-galactosidase as the internal control. Retinoid activity was normalized relative to that of retinoic acid and is expressed as potency (EC50), which is the concentration of retinoid required to produce 50% of the maximal observed response, and efficacy (%), which is the maximal response observed relative to that of retinoic acid at 10$^{-5}$M.

The receptor expression vectors used in the cotransfection assay have been described previously [pRShRAR-α: Giguere et al., Nature 330:624–629 (1987); pRShRAR-β and pRShRAR-γ: Ishikawa et al., Mol. Endocrinol. 4:837–844 (1990); retinoid X receptor-alpha (RXR-α) [see Mangelsdorf et al., in Nature 345: 224–229 (1990)], retinoid X receptor-beta (RXR-β) and retinoid X receptor-gamma (RXR-γ) [see Mangelsdorf et al., Genes and Development 6:329–344 (1992)]. A basal reporter plasmid ΔMTV-LUC [Hollenberg and Evans, Cell 55:899–906 (1988)] containing two copies of the TRE-palindromic response element 5'-TCAGGTCATGACCTGA-3' [SEQ ID No 2; see Umesono et al., Nature 336:262–265 (1988)] was used in all transfections for the retinoid receptors.

The bacterial expression vector for PET-8c-RAR-α used in the competitive binding assay has been reported [Yang et al., Proc. Natl. Acad. Sci. USA 88:3559–3563 (1991)]. Similar expression vectors employing the PET-8c vector system [Studier et al., Methods in Enzymology 185:60–69 (1990)] were constructed for RAR-β and RAR-γ.

Figure 1:
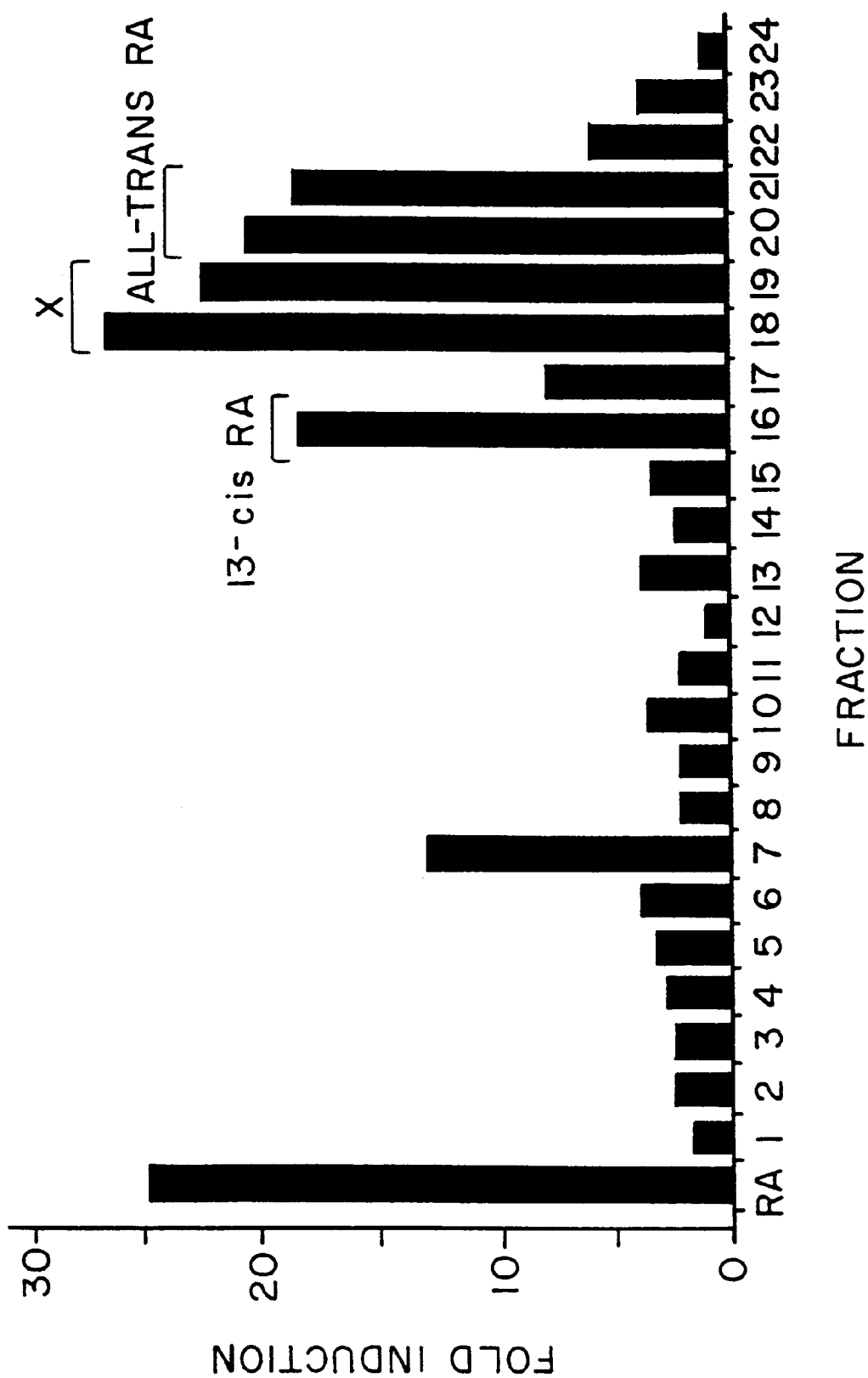
FIG. 1 is a transactivation profile of various HPLC fractions obtained from retinoic acid (RA)-treated S2 cells.

The transactivation profile of RXR-alpha with the various HPLC fractions containing various retinoic acid isomers and/or metabolites is shown in FIG. 1. These data reveal two distinct regions of activity, one relatively early (fraction 7) and a second broader region of activity (fractions 16–21) that elutes considerably later. The all-trans-retinoic acid coelutes in fractions 20 and 21 (FIG. 1) and is the major U.V. absorbing material present in the cell extracts. However, the activity profile demonstrates that, in addition to all-trans-retinoic acid, there are active components that must be derived from, or induced by, all-trans-retinoic acid that activate RXR.

Figure 2A:
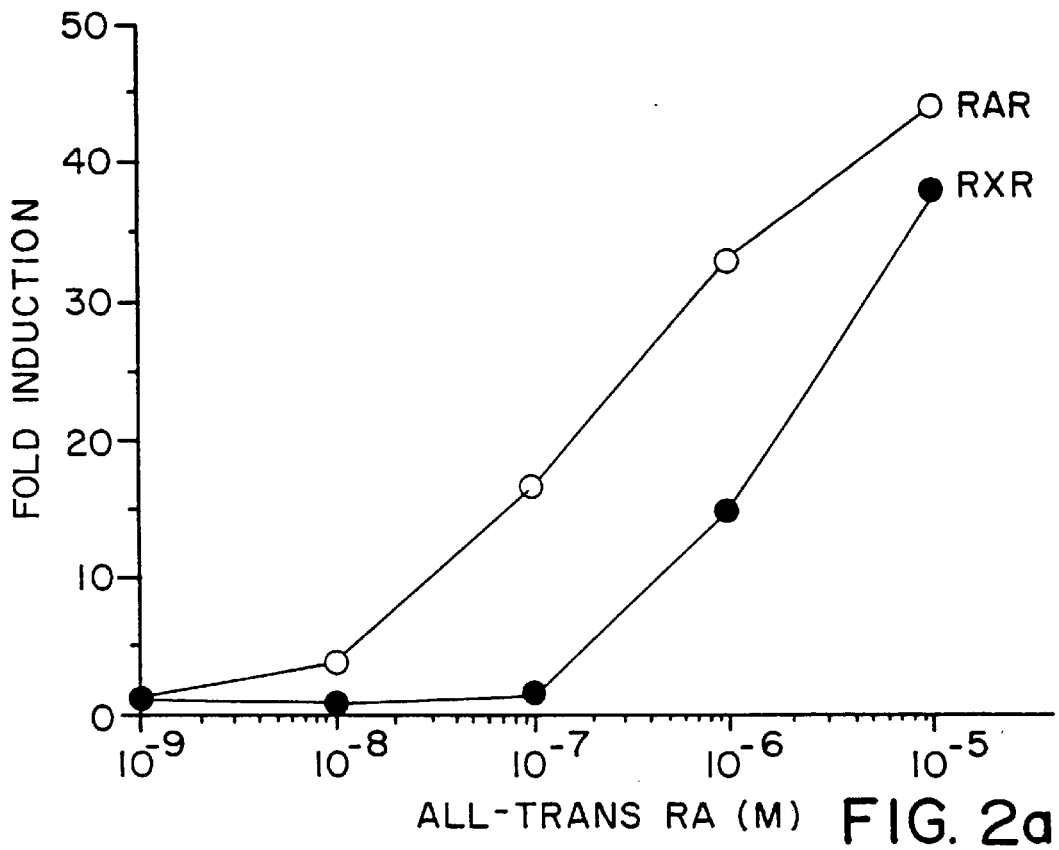
FIG. 2 panel a is a comparison of the transactivation profile of all-trans-retinoic acid (RA) on RAR-alpha and RXR-alpha.
Figure 2B:
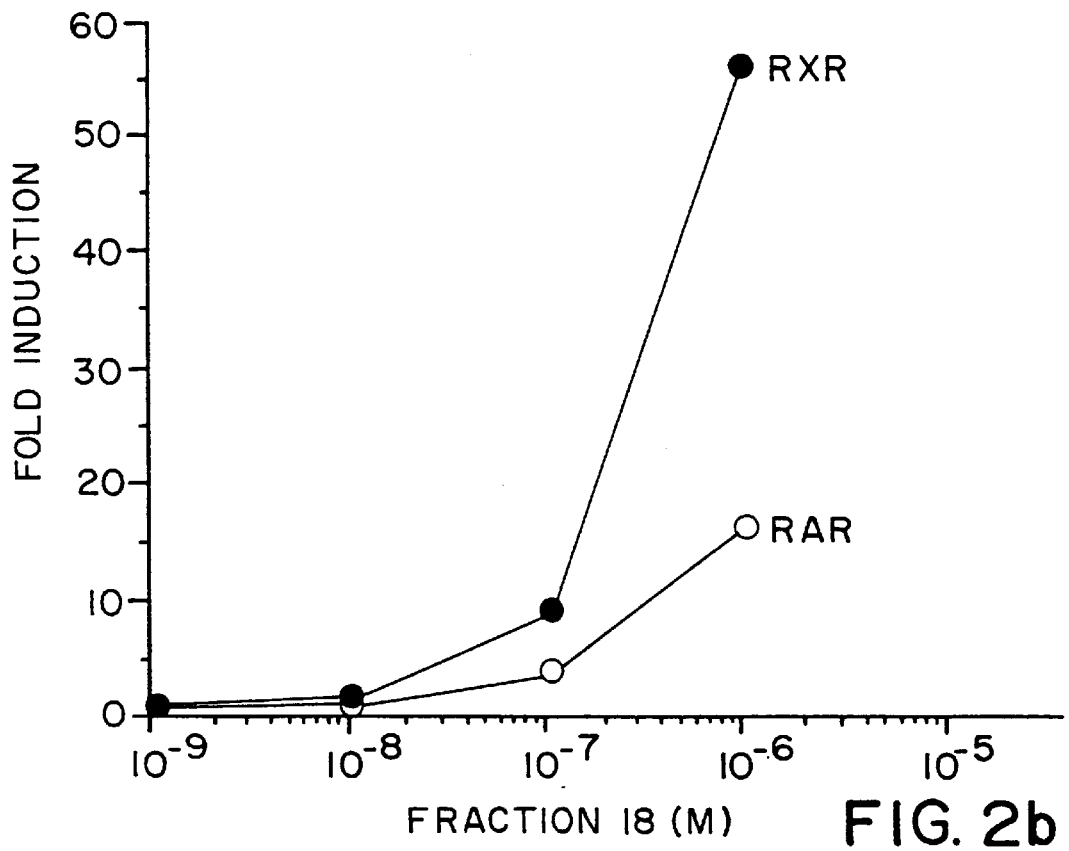

To identify potential compounds that would be as effective or more active than all-trans-retinoic acid, one must take into account not only the activity of the individual fractions, but also their concentrations. All active fractions were therefore reassayed over a broad range of concentrations, taking into account the relative concentrations of the individual fractions. To determine the relative concentrations of the fractions, the following initial assumptions were made: 1) the active fractions are retinoic acid metabolites and 2) the molar extinction coefficient of the various active fractions is relatively similar (i.e., within a factor of two). This assumption is supported by values reported in the literature for a large number of retinoids. A comparison of the transactivation profile of all-trans-retinoic acid (i.e., fraction 20) on RAR-alpha and RXR-alpha is shown in FIG. 2a. Although the maximal activation (i.e., efficacy) of RAR and RXR with retinoic acid is similar, RAR is more sensitive by a factor of approximately 10 fold (i.e., 10 fold more potent). In contrast, analysis of the various fractions produced as describes above demonstrates that fraction 18 is considerably more active on RXR than RAR (see FIG. 2b). These data suggest that a metabolic product present in S2 cells pretreated with retinoic acid is a more potent activator of the RXR subfamily than the RAR subfamily.

Example 2

Identification of 9-cis retinoic acid as a transactivator of RXR

Two observations suggest that fraction 18 (peak X, see FIG. 1) is a cellular metabolite of all-trans-retinoic acid. First, extracts of Schneider cells grown in the absence of all-trans-retinoic acid do not exhibit peak X. Second, when cells are exposed to all-trans-retinoic acid, X appears in a time-dependent fashion.

Therefore, to chemically identify X, fraction 18 was subjected to chemical derivatization, high performance liquid chromatography (HPLC) and gas chromatography/mass spectrometry (GC/MS). It was found that upon methylation with diazomethane, the retention time of peak X shifts dramatically (i.e., from 10.2 minutes to 19.5 minutes under the HPLC conditions used). This indicates that the compound(s) corresponding to peak X has a free carboxyl group. When methylated X was analyzed by GC/MS, the electron impact mode revealed that X gives rise to a molecular ion at m/z 314, corresponding to that of a retinoic acid methyl ester. This suggests that X is a stereoisomer of retinoic acid. To determine which isomer X represents, the retention time of X was compared with that of 9-cis-, 11-cis- and 13-cis-retinoic acid. It was found that X coelutes with authentic 9-cis-retinoic acid. Furthermore, the methyl ester of X coelutes with 9-cismethylretinoate, and when the methyl ester of X is reduced to the alcohol with lithium aluminum hydride, the resulting product coelutes with authentic 9-cis-retinol.

For GC/MS analysis, methylated retinoic acid isomers were dissolved in hexane. The sample was injected via a falling needle injector (280° C.) into a 30 m×0.32 mm fused silica DB5 capillary column (J+J scientific) inserted directly into the ion source of a VG Trio-1000 mass spectrometer operating in electron impact mode (70 eV). The sample was eluted with a temperature gradient (200–300° C., 10° C. $min^{-1}$)

Finally, the mass spectrum of authentic 9-cis-retinoic acid methyl ester and that of methylated peak X are found to be identical. Taken together these analyses establish that peak X represents 9-cis-retinoic acid. Although earlier work indicated the presence of 9-cis-retinol in fish liver, it was not clear whether 9-cis-retinoic acid existed in vivo (i.e., whether 9-cis-retinoic acid is a physiological compound). To find out if 9-cis-retinoic acid exists in vivo, mouse liver and kidney tissues were extracted. These tissues were selected because they contain a broad spectrum of retinoid metabolites and also express RXR. Prior to extraction, radiolabeled 9-cis-retinoic acid was added to the kidney homogenate to serve as an internal standard. Extracts were first fractionated on a reverse phase column (Waters Novo pak 300 mm $C_{18}$ analytical column at a flow rate of 1 ml/min) using mobile phase G.

Fractions from the kidney extracts containing radioactive internal standard were rechromatographed on a second $C_{18}$ column using mobile phase H. This procedure gave a small, but distinct absorbance peak which co-migrated with authentic 9-cis-retinoic acid.

Similarly, liver extract was fractionated on a reverse phase column and eluted with mobile phase G. However under the conditions employed, 9-cis-retinoic acid eluted with all-trans-retinol (which is abundantly present in the liver). To separate these two retinoids, this fraction was methylated with diazomethane and then reanalyzed by HPLC employing mobile phase C. This approach resulted in a distinct peak coeluting with the authentic methyl ester of 9-cis-retinoic acid.

To rule out the possibility that 9-cis-retinoic acid had formed during the extraction procedure from all-trans-retinoic acid, liver tissue homogenate was spiked with tritiated all-trans-retinoic acid. Subsequent HPLC fractionation revealed that 94% of the radioactivity still resided in all-trans-retinoic acid, approximately 5% in 13-cis-retinoic acid and 1% or less in 9-cis-retinoic acid. Based on peak area integration the concentrations of 9-cis-ratinoic acid in liver and kidney are estimated to be ~4 ng, and ~4 ng, respectively, per g of wet weight. This indicates that endogenous 9-cis-retinoic acid is not formed from all-trans-retinoic acid during extraction. In conclusion, these experiments establish that 9-cis-retinoic acid is a naturally occurring retinoic acid isomer.

Example 3

Transactivation Profile of Retinoid Isomers on RXR and RAR

The establishment that peak X represents a stereoisomer of all-trans-retinoic acid suggested that the various retinoid isomers may have different retinoid receptor activation profiles. To further analyze the ability of retinoic acid isomers to modulate the transcriptional properties of RXR-alpha and RAR-alpha, the four major photoisomers of all-trans-retinoic acid were identified and assayed for the ability to transactivate RXR and RAR. FIG. 3 shows the dose response curves for 13-cis-, 11-cis-, 9-cis- and all-trans-retinoic acid for both RAR-alpha and RXR-alpha.

Figure 3B:
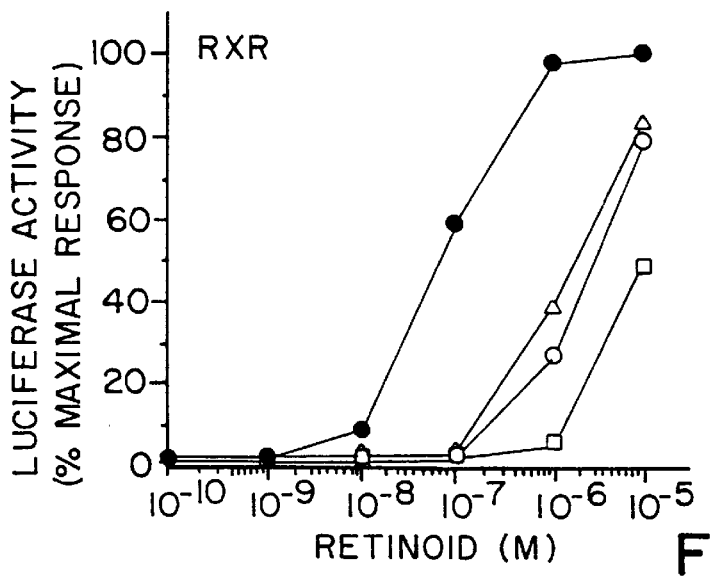

Of the four major isomers of retinoic acid, 9-cis-retinoic acid is seen to be the most potent and efficacious activator of RXR-alpha in both insect S2 cells (see FIG. 3A) and mammalian CV-1 cells (see FIG. 3B). The maximal response (EC50 value) is $10^{-8}$M and $5 \times 10^{-8}$M, respectively. The observed rank order of potency for the different isomers is the same in both cell lines. 9-cis-retinoic acid is approximately 40 fold more potent as an activator of RXR than 11-cis-, 13-cis- or all-transretinoic acid. These transactivation data strongly suggest that 9-cis-retinoic acid is an endogenous RXR-alpha activator.

Figure 3C:
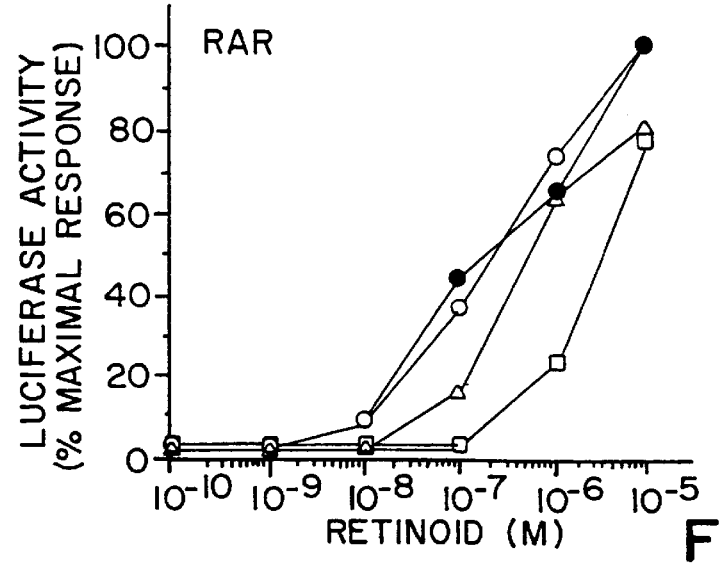

In contrast, 9-cis-retinoic acid is equipotent to all-trans-retinoic acid as an activator of RAR-alpha (FIG. 3C). The EC50 value for 9-cis-retinoic acid on RAR-alpha is $2 \times 10^{-7}$M. 9-cis-retinoic acid is the most potent RXR-alpha ligand to be tested to date.

Similarly, transactivation of other isoforms of RXR (i.e., RXR-beta, RXR-gamma) and RAR (i.e., RAR-beta, RAR-gamma) by 9-cis-retinoic acid was also examined. 9-cis-retinoic acid was also found to be a potent activator of these isoforms as well, as shown in Table 1:

TABLE 1

| | $EC_{50}$ * (nM) | |
|---|---|---|
| Receptor | All-trans-retinoic Acid | 9-cis-retinoic Acid |
| RAR-α | 3861 ± 13 | 327 ± 30 |
| RAR-β | 152 ± 12 | 95 ± 13 |
| RAR-γ | 48 ± 8 | 61 ± 5 |
| RXR-α | 1174 ± 26 | 255 ± 17 |
| RXR-β | 1841 ± 26 | 218 ± 17 |
| RXR-γ | 1369 ± 26 | 254 ± 19 |

*Mean ± SEM

Example 4

9-cis retinoic acid Binds Directly to RXRs

The ability of 9-cis-retinoic acid to transactivate RXR-alpha suggested testing to see whether 9-cis-retinoic acid was also capable of binding directly to RXRs. RXR-alpha was expressed in baculovirus and was shownto have biochemical properties that were identical to the mmalian expressed protein. The baculovirus expressed rote in had a molecular weight of 51,000, reacted specifically with RXR-alpha antibody and was capable of binding in vitro to DNA sequences that have been previously shown to be specific RXR response elements [i.e. CRBPII, see Mangelsdorf et al., Cell 66:555 (1991); apolipoprotein AI gene, see Rottman et al., Mol. Cell Biol. 11:3814 (1991)].

Figure 4A:
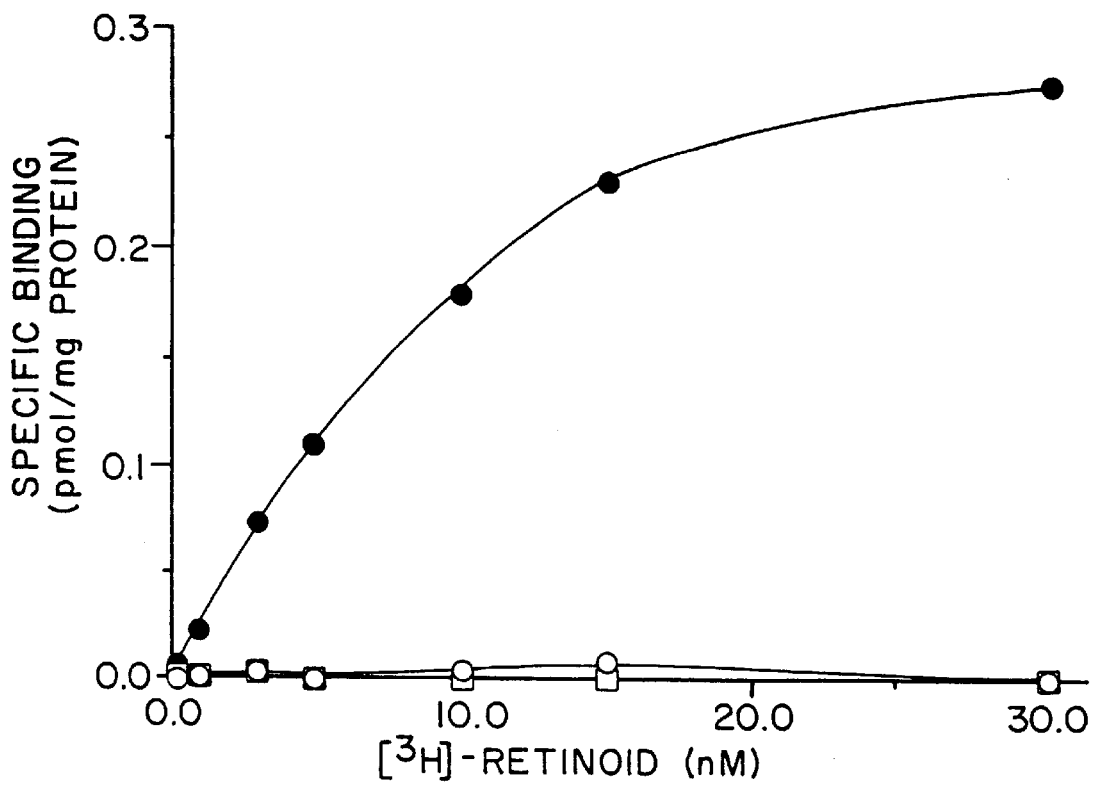
Figure 4B:
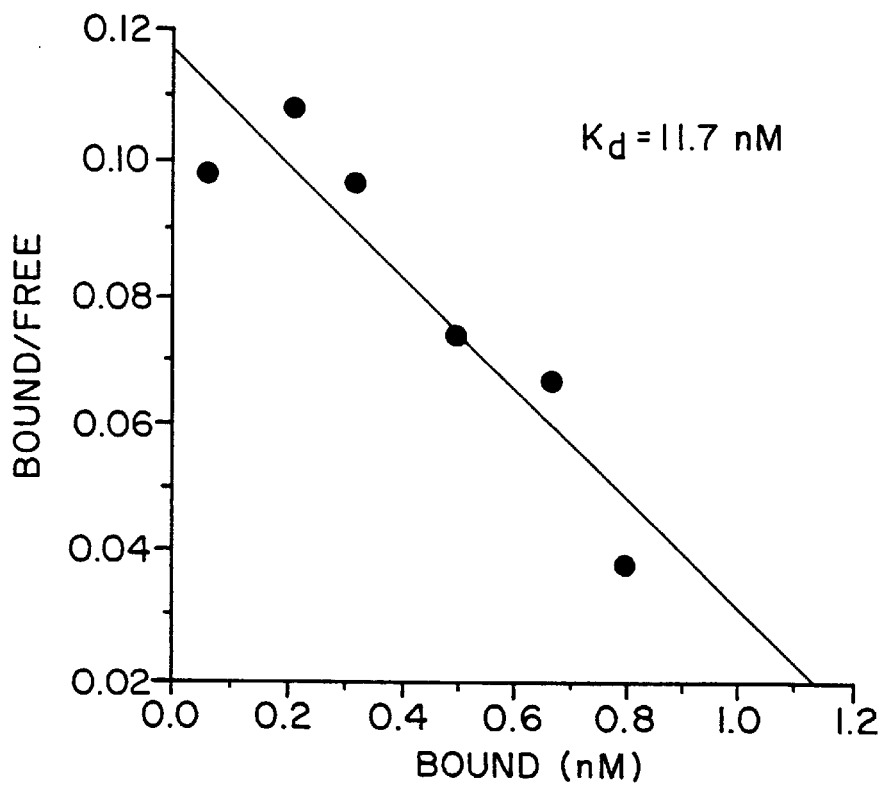

To characterize the ligand binding characteristics of 9-cis-retinoic acid to baculovirus-derived RXR, saturation binding analysis was carried out (see FIG. 4). Radiolabelled 9-cis-retinoic acid binds specifically to RXR-alpha in a saturable manner. Scatchard analysis suggests a single high affinity binding site with a Kd value of 11.7 nM (see FIG. 4b). Under identical binding conditions [$^3$H]-all-trans-retinoic acid did not bind to RXR-alpha (see FIG. 4a). In addition, 9-cis-retinoic acid was also capable of binding specifically to RAR-alpha as a high affinity ligand. 9-cis-retinoic acid did not bind to mock baculovirus extracts (i.e., control extracts from cells that do not express RXRs).

Similarly, binding studies were also carried out with other isoforms of RXR (i.e., RXR-beta, RXR-gamma), other isoforms of RAR (i.e., RAR-beta, RAR-gamma), and cellular reinoic acid binding protein (CRABP) with all-trans-retinoic acid and 9-cis-retinoic acid. While all-trans-retinoic acid is known to bind to each of these "receptors", 9-cis-retinoic acid was also found to bind to the other isoforms of retinoid receptors (but not to the cellular retinoic acid binding protein, CRABP), as shown in Table 2:

TABLE 2

| | Kd (nM) | |
|---|---|---|
| Receptor | All-trans-retinoic Acid | 9-cis-retinoic Acid |
| RAR-α | 0.4 | 0.3 |
| RAR-β | 0.4 | 0.2 |
| RAR-γ | 0.2 | 0.8 |
| RXR-α | No binding | 1.5 |
| RXR-β | No binding | 2.1 |
| RXR-γ | No binding | 1.9 |
| CRABP | 20 | >100 |

The properties of many members of the steroid hormone receptor superfamily have been characterized and defined using DNA cellulose chromatography [see, for example, Pike and Haussler, Proc. Natl. Acad. Sci. USA 76:5485 (1979) and Pike et al., J. Biol. Chem. 258:1289 (1983)]. Receptors, such as the VDR, have been shown in the presence of their cognate ligand to bind to DNA-cellulose [see, for example, Allegretto et al., J. Biol. Chem. 262:1312 (1987)] with high affinity and the ligand-receptor complex elutes with a salt gradient. A DNA-cellulose column profile of the baculovirus expressed RXR that had been prelabeled with [$^3$H]-9-cis-retinoic acid is shown in FIG. 5. The two different profiles represent 1) the total amount of [$^3$H]-9-cis-retinoic acid bound and 2) the level of binding that remains in the presence of 200-fold excess of cold (i.e. non-labeled 9-cis-retinoic acid).

There is a peak of radioactivity (marked in the Figure by an arrow) that elutes off the DNA-cellulose column at 0.15M KCl. This elution profile is similar to that seen with RARc in the presence of [ H]-all-trans-retinoic acid. A 200 fold excess of cold ligand (i.e. non-specific) is capable of competing greater than 90% of the total radioactivity bound, demonstrating that the radioactivity in the peak fractions is 9-cis-retinoic acid specifically bound to RXR.

The radioactivity eluted off the column was extracted with organic solvent and subjected to HPLC analysis.

Inspection of FIG. 5b makes it clear that the radioactivity bound to RXR co-chromatographs with authentic 9-cis-retinoic acid. This observation further confirms that [$^3$H]-9-cis-retinoic acid is the species bound to RXR.

To demonstrate that the protein contained in the peak fractions is indeed RXR, these fractions (labelled 1–15 in FIG. 5a) were subjected to immunoblot analysis using an RXRα specific polyclonal antiserum (see FIG. 5a, top). All fractions containing radioactivity display a distinct RXRα band at a $M_r$ of 51,000. When a similar experiment was conducted with a baculovirus mock extract, no specific radioactivity was retained on the column. Taken together, these data strongly suggest that 9-cis-retinoic acid is capable of binding specifically to RXR.

Protein samples were resuspended in 2X sample buffer [Laemelli, Nature Vol. 227:680 (1970)] and boiled for 5 minutes prior to loading onto a 9% SDS polyacrylamide gel. After electrophoretic separation the gels were electroblotted onto nitrocellulose membranes (Scheicher and Schuell) for 8 hours at 30 volts using a Hoeffer electro-transfer apparatus. Membranes were then incubated in 10% isopropanol, 10% acetic acid for 15 minutes, washed 5 minutes in deionized H$_2$O and 5 minutes in T-TBS buffer (10 mM Tris pH 7.5, 150 mM NaCl and 0.5% Triton X-100). The membranes were blocked in 5% nonfat milk in T-TBS for 1 hour. The remainder of the protocol was adapted from the Amersham ECL (Enhanced Chemiluminescence) Western blotting detection system kit. The primary antibody was a rabbit polyclonal serum raised against a synthetic peptide corresponding to amino acids 214–229 of hRXRα [Kliewer et al., Proc. Natl. Acad. Sci. USA 89:1448–1452 (1992)]. The primary antiserum was diluted 1:5000 in T-TBS. The secondary antibody (Donkey anti rabbit IgG conjugated to horseradish peroxidase, Amersham) was used at a dilution of 1:2500.

Example 5

Effects of topical application of 9-cis-retinoic acid (compared with all-trans-retinoic acid) on horn-filled utriculus size in the Rhino Mouse All-trans-retinoic acid is known to influence cell differentiation and exert profound therapeutic benefits in the treatment of keratinization disorders [Elias et al., Arch. Dermatol. Vol. 117:160–180 (1981)]. Mezick et al. [see J. Invest. Derm. Vol. 83:110–113 (1984)] demonstrated that topical treatment of rhino mice (hr hr) with all-trans-retinoic acid could reduce keratinized pilosebaceous structures (horn-filled utriculus). This animal test model was used to evaluate the "antikeratinizing" effects of 9-cis-retinoic acid. Results are summarized in Table 3:

TABLE 3

|  | Pilosebaceous structure size | (% red'n) |
| --- | --- | --- |
| Vehicle Control | 178 μm |  |
| 9-cis-retinoic acid, |  |  |
| 0.1% | 52 μm | (−74%) |
| 0.01% | 72 μm | (−64%) |
| All-trans-retinoic acid, |  |  |
| 0.1% | 44 μm | (−78%) |
| 0.01% | 50 μm | (−75%) |

9-cis-retinoic acid reduced the mean utriculi diameter after 14 days of topical application. These results demonstrate that topical application of 9-cis-retinoic acid over a 14 day period can reduce keratinized pilosebaceous structures (horn-filled utriculus) in Rhino mouse skin. Reduction in the mean utriculi diameter by 9-cis-retinoic acid was comparable to that observed with all-trans-retinoic acid.

Example 6

Effects of 9-cis-retinoic acid (compared with all-trans-retinoic acid) on differentiation of HL60 cells Retinoids are known to differentiate human promyelocytic leukemia cells. Differentiation of HL60 cells (a model system for promyelocytic leukemia) can be assessed by Nitro Blue Tetrazolium (NBT) dye reduction (superoxide anion generation) and by measurement of upregulation of the gene encoding the β subunit of the leukocyte adherence receptor, CD18 (J.B.C. vol. 263 No. 27, pp. 13863–13867).

The EC-50 for 9-cis-retinoic acid-mediated differentiation, as determined by NBT after 6 days treatment, was 0.2 μM compared to 2 μM for all-trans-retinoic acid. Maximal effects (efficacies) were comparable, and CD18 was up-regulated by both ligands. Alpha-interferon potentiated both all-trans-retinoic acid and 9-cis-retinoic acid-mediated differentiation, as determined by NBT.

HL60R cells have been shown to be resistant to differentiation by all-trans-retinoic acid, probably related to a mutation in the retinoic acid receptor-alpha gene. This cell line was found to be resistant to differentiation (NBT) by both all-trans-retinoic acid and 9-cis-retinoic acid at concentrations up to 10 μM.

9-cis-retinoic acid effects differentiation of HL60 cells as evidenced by NBT and up-regulation of CD18. Compared with all-trans retinoic acid, 9-cis retinoic acid is more potent with similar efficacy.

Example 7

Effects of 9-cis-retinoic acid (compared with all-trans-retinoic acid) on in vitro proliferation of melanoma cell lines All-trans-retinoic acid and several synthetic analogs (retinoids) have been shown to prevent the development of benign and malignant, chemically induced epithelial tumors in vivo [Sporn et al., Fed. Proc. Vol. 35:1332–1338 (1976)]. Lotan et al. (J. Natl. Cancer, Vol. 60:1035–1041, 1978) found that all-trans-retinoic acid inhibited the growth of several tumor cell lines in vitro. In view of these earlier findings, it was of interest to evaluate the growth inhibitory properties of 9-cis-retinoic cid.

9-cia-retinoic acid inhibited the growth of the urine melanoma cell line Clone M3 in a concentration dependent manner, as follows:

|  | % Growth inhibition (Conc added) | |
| --- | --- | --- |
|  | 1 μM | 0.01 μM |
| 9-cis-retinoic acid | −85% | −49% |
| all-trans-retinoic acid | −94% | −48% |

Similarly, 9-cis retinoic acid inhibited the growth of the human primary metastatic melanoma cell line c81-46c in a concentration dependent manner.

|  | % Growth inhibition (Conc added) | |
| --- | --- | --- |
|  | 1 μM | 0.01 μM |
| 9-cis-retinoic acid | −45% | −28% |
| all-trans-retinoic acid | −44% | −17% |

In summary, 9-cis-retinoic acid has been shown to inhibit the in vitro proliferation of murine melanoma cell line Clone M3 and human metastatic melanoma cell line c81-46c in a concentration dependent manner. 9-cis-retinoic acid has an equal inhibitory effect on these cells as compared to all-trans-retinoic acid.

Example 8

Effects of 9-cis-retinoic acid (compared with all-trans-retinoic acid) on differentiation of F9 cells Retinoids are known to differentiate mouse teratocarcinoma cells (F9). Differentiation of F9 cells is specifically associated with irreversible changes in morphology and induction of the biochemical marker alkaline phosphatase (ALP) and tissue plasminogen activator (tPA) (Biochem. J. Vol. 274:673–678).

Both all-trans-retinoic acid and 9-cis-retinoic acid induced differentiation of F9 cells into partial endoderm-like cells as indicated by irreversible changes in cellular morphology. All-trans-retinoic acid was 40 times more potent than 9-cis-retinoic acid in inducing ALP, maximal responses were similar.

The response of tissue plasminogen activator factor was less for 9-cis-retinoic acid than for all-trans-retinoic acid. At a concentration of 1 $\mu$M of 9-cis-retinoic acid (or all-trans-retinoic acid), increased cellular activities of tPA by 0.48±0.05 and 0.80±0.08, respectively were observed. This effect was concentration-dependent.

In summary, 9-cis-retinoic acid promoted differentiation of F9 cells as evidenced by changes in morphology and marker enzyme activities. Compared with all-trans-retinoic acid, 9-cis-retinoic acid was less potent with regard to both enzyme markers. Efficacy was comparable with ALP but indeterminate for tPA.

Example 9

Effects of 9-cis-retinoic acid (compared with all-transretinoic acid) on differentiation of keratinocytes Retinoids are known to inhibit squamous cell differentiation of cultured normal human epidermal keratinocytes (NHEK534 cell line), as judged by morphological alterations and inhibition of induction of transglutaminase (Type I) (J. Biol. Chem. Vol. 261:15097, 1986; Lab. Invest. Vol. 56:654, 1987).

Both all-trans-retinoic acid and 9-cis-retinoic acid inhibited squamous cell differentiation in a concentration dependent manner as judged by morphological changes and by transglutaminase activity. The EC50s for inhibition of differentiation by all-trans-retinoic acid and 9-cis-retinoic acid were identical (20±2.8 nM). 9-cis retinoic acid and all-trans-retinoic acid EC50s and potencies were nearly identical for effects on transglutaminase activities.

In summary, like all-trans-retinoic acid, 9-cis-retinoic acid inhibits morphological differentiation of NHEK534 cells and induction of transglutaminase activity.

Example 10

Synthesis of 9-phenyl-9-cis-retinoic acid

To a solution of 44 mg (0.10 mmole) of the following phosphonate reagent:

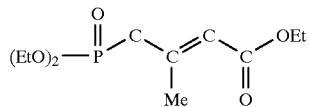

in THF (0.5 ml) at room temperature was added NaH (60% in oil, 5 mg; 0.13 mmole) and the mixture stirred at that temperature for 10 minutes. To this, 26 mg (0.08 mmole) of the aldehyde:

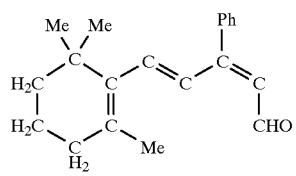

in THF (0.5 ml) was added at room temperature and the mixture allowed to stir for 30 minutes. Aqueous workup in the usual manner (NH$_4$Cl (aq) , H$_2$O, brine, MgSO$_4$) gave a mixture of 9-phenyl-9-cis ester and 9-phenyl-9,13-dicis ester (30 mg, 92%) (the calculated ratio of 9-cis: 9,13-dicis =4:1).

ethyl ester of 9-phenyl-9-cis-retinoic acid

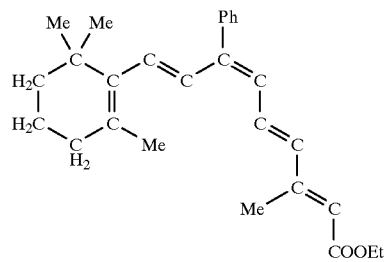

ethyl ester of 9-phenyl-9,13-dicis-retinoic acid

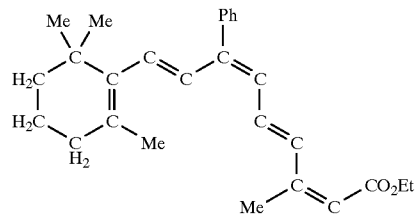

To a mixture of 9-cis and 9,13-dicis ester (20 mg, 0.05 mmole) in methanol (0.7 ml) and H$_2$O (0.7 ml) at 25° C. was added KOH (14.3 mg, 0.25 mmole). Consequently, the mixture was heated to 70° C. for 2 hours. The reaction was then cooled down to 0° C., diluted with 10 ml of diethyl ether), and acidified with HCl (0.12M in HCl, 2.17 ml). Aqueous workup in the usual manner (H$_2$O, brine, MgSO$_4$) gave a mixture of 9-cis and 9,13-dicis acid. Flash column chromatography (silica, 13% ethyl acetate in benzene) gave pure 9-phenyl-9-cis retinoic acid (14.5 mg. 100%).

The $^1$HNMR spectrum of 9-phenyl-9-cis retinoic acid is as follows:

$^1$HNMR (400 mHz), CDCl$_3$) δ 7.4–7.3 (m, 5H, aromatic), 7.20 (dd, J=16, 12 Hz, 1H, olefinic), 6.60 (d, J=16 Hz, 1H, olefinic), 6.38 (d, J=16 Hz, 1H, olefinic), 6.25 (d, J =12 Hz, 1H, olefinic), 6.15 (d, J=16 Hz, 1H, olefinic), 5.80 (s. 1H, olefinic), 2.48 (s. 3H, CH$_3$l, 2.05 (t. J=5Hz, 2H, CH$_2$), 1.79 (s, 3H, CH$_3$), 1.70–1.40 (m, 4H, CH$_2$—CH$_2$), 1.00 (s, 6H, 2×CH$_3$).

9-phenyl-9-cis RA: TLC Rf 0.23 (13% ethyl acetate in Benzene)

Example 11

Synthesis of 4-hydroxy-9-cis-retinoic acid

To a solution of 9-cis-retinoic acid (51 mg, 0.17 mmole) in 1.4-dioxane (2 ml) was added SeO$_2$ (19 mg, 0.17 mmole)

at 60° C. The solution was allowed to stir at that temperature for 3 hours. The reaction mixture was then filtered through a silica bed. The filtrate was concentrated and the residue subjected to flash column chromatography (silica, 75% ether in petroleum ether) to afford 4-OH-9-cis-retinoic acid (21 mg., 40% yield), which is characterized as follows: Oil; TLC Rf=0.25 (silica, 75% ether in petroleum ether); $^1$HNMR (400 MHz, CDCl$_3$) δ 7.08 (dd, J=16, 12 Hz, 1H, olefinic); 6.64 (d, J=16 Hz, 1H, olefinic), 6.21 (d, J=16 HZ, 1H, olefinic), 6.20 (d, J=16 Hz, 1H, olefinic); 6.04 (d, J=12 Hz, olefinic), 5.79 (s, 1H, olefinic), 4.02 (t, J=5 Hz, 1H, CH—O), 2.18 (s, 3H, CH$_3$), 2.02 (s, 3H, CH$_3$), 1.82 (s, 3H, CH$_3$), 2.0–1.6 (m, 4H, CH$_2$—CH$_2$), 1.05, 1.03 (2×s, 2×3H, 2×CH$_3$).

Example 12

Synthesis of 4-keto-9-cis-retinoic acid

To a solution of 4-hydroxy-9-cis-retinoic acid (16 mg, 0.05 mmole) in CH$_2$Cl$_2$ (1.5 ml) was added Dess-Martin reagent [see Dess and Martin in J. Org. Chem. 48:4155 (1983)] (42 mg, 0.1 mmole) in one portion at 25° C. After stirring for 5 minutes, the mixture was diluted with 10 ml of ether and to this was added saturated aqueous NaHCO$_3$ (5 ml) containing Na$_2$SO$_3$ (55 mg). The mixture was stirred for 20 minutes to dissolve the solid and the layers separated. The ether layer was washed with H$_2$O (2×5 ml), brine (5 ml) and dried (MgSO$_4$). The solvent was recovered under reduced pressure and residue was subjected to flash column chromatography (silica, 60% ether in Hexane) to give 4-keto-9-cis-retinoic acid (14 mg. 90%), characterized as follows: TLC rf=0.6 (silica, 80% ether in hexane); $^1$HNMR (400 mHz, CDCl$_3$) δ 7.05 (dd, J=16, 12 Hz, 1H, olefinic), 6.82 (d, J=16 Hz, 1H, olefinic), 6.32 (d, J=16 Hz, 1H, olefinic), 6.30 (d, J=16 Hz, 1H, olefinic), 6.20 (d, J=12 Hz, 1H, olefinic), 5.80 (s, 1H, olefinic), 2.5 (t, J=7 Hz, 2H, CH$_2$—CO), 2.31 (s, 3H, CH$_3$), 2.01 (s, 3H, CH$_3$), 1.9 (s, 3H, CH$_3$), 1.89 (m, 2H, CH$_2$), 1.20 (s, 6H, 2×CH$_3$).

Example 13

In vitro evaluation of 9-phenyl-9cis-retinoic acid, 4-hydroxy-9-cis-retinoic acid and 4-keto-9-cis-retinoic acid The potency and efficacy of the compounds described in Examples 10, 11 and 12 were determined (as described in Example 1—under the heading "Cotransfection Assay in CV-1 Cells". The results are presented in Table 4:

TABLE 4

| Receptor | 9-cis-retinoic acid | | 9-phenyl-9-cis-retinoic acid | | 4-hydroxy-9-cis-retinoic acid | | 4-keto-9-cis-retinoic acid | |
|---|---|---|---|---|---|---|---|---|
| | Potency (nM) | Efficacy | Potency (nM) | Efficacy | Potency (nM) | Efficacy | Potency (nM) | Efficacy |
| RXRα | 88 | 170% | 210 | 76% | 1700 | 161% | 520 | 104% |
| RXRβ | 61 | 106% | 44 | 88% | 650 | 143% | 1300 | 105% |
| RXRγ | 360 | 137% | 290 | 77% | 1700 | 115% | 1100 | 133% |
| RARα | 99 | 94% | >10,000 | <2% | 380 | 65% | 200 | 50% |
| RARβ | 22 | 97% | 880 | 39% | 160 | 71% | 26 | 67% |
| RARγ | 43 | 108% | 250 | 59% | 180 | 81% | 55 | 107% |

While the invention has been described in detail with reference to certain preferred embodiments thereof, it will be understood that modifications and variations are within the spirit and scope of that which is described and claimed.

That which is claimed is:

1. A method for in vivo modulation of a non-malignant skin disorder in a subject, wherein said non-malignant skin disorder is selected from the group consisting of aging, wrinkingling, acne, keratinization, differentiation, and proliferation disorders, said method comprising administering to said subject an effective amount of 9-cis-retinoic acid or pharmaceutically acceptable carriers containing same.

2. A method for in vivo modulation of the development of benign tumors in the skin of a subject, said method comprising administering to said subject an effective amount of 9-cis-retonic acid or pharmaceutically acceptable carriers containing same.

* * * * *